United States Patent
Ueda et al.

[19]

[11] Patent Number: 6,075,610

[45] Date of Patent: Jun. 13, 2000

[54] METHOD AND APPARATUS FOR MEASURING INTERNAL PROPERTY DISTRIBUTION

[75] Inventors: Yukio Ueda; Yutaka Tsuchiya; Kazuyoshi Ohta, all of Hamamatsu, Japan

[73] Assignee: Hamamatsu Photonics K.K., Hamamatsu, Japan

[21] Appl. No.: 08/853,879

[22] Filed: May 9, 1997

[30] Foreign Application Priority Data

| May 10, 1996 | [JP] | Japan | 8-140711 |
| Nov. 29, 1996 | [JP] | Japan | 8-334674 |

[51] Int. Cl.[7] .................................................. G01N 21/49
[52] U.S. Cl. ......................... 356/432; 356/343; 600/310
[58] Field of Search .................................. 600/310, 316, 600/322, 323, 328, 339, 473, 476; 356/337, 342, 343, 432

[56] References Cited

U.S. PATENT DOCUMENTS

| 5,070,455 | 12/1991 | Singer et al. ..................... 364/413.19 |
| 5,137,355 | 8/1992 | Barbour et al. ........................ 356/237 |
| 5,517,987 | 5/1996 | Tsuchiya ................................ 128/633 |
| 5,610,399 | 3/1997 | Muller et al. . | |
| 5,676,142 | 10/1997 | Miwa et al. ............................ 128/633 |

FOREIGN PATENT DOCUMENTS

| 692708A2 | 1/1996 | European Pat. Off. . |
| 5-502393 | 4/1993 | Japan . |
| 2228314 | 8/1990 | United Kingdom . |
| 89/12223 | 12/1989 | WIPO . |
| 93/25145 | 12/1993 | WIPO . |

OTHER PUBLICATIONS

Jiang, et al, "Simultaneous reconstruction of optical absorption and scattering maps in turbid media from near–infrared frequency–domain data", Optics Letters, Oct. 15, 1995, vol. 20, No. 20, pp. 2128–2130.

Garber et al, "Imaging of Multiple Targets in Dense Scattering Medium", SPIE, vol. 2570, pp. 219–234.

Chang et al, Imaging Diffusive Media Using Time–Independent and Time–Harmonic Sources; Dependence of Image Quality on Imaging Algorithms, Target Volume, Weight Matrix, and View Angles, SPIE, vol. 2389, pp. 448–464.

(List continued on next page.)

*Primary Examiner*—Robert H. Kim
*Assistant Examiner*—Zandra V. Smith
*Attorney, Agent, or Firm*—Pillsbury Madison & Sutro LLP

[57] ABSTRACT

A method for measuring an internal property distribution which includes making measurement light incident from a plurality of light incidence positions on a surface of a measured object, detecting the measurement light that has passed through the object, successively or simultaneously, at at least one light detection position out of a plurality of light detection positions on the surface of the object. A plurality of measurement values obtained by a plurality of combinations of the light incidence position and said light detection position are extracted. A mean value of the measured values are calculated to obtain a reference value and a change amount of a predetermined internal property in each of the plurality of regions of the object are calculated using the plurality of measured values obtained. The reference value thereby establishing an internal property change amount distribution in the object.

26 Claims, 21 Drawing Sheets

OTHER PUBLICATIONS

Pogue et al, "Forward and Inverse Calculations for 3–D Frequency–Domain Diffuse Optical Tomography", SPIE, vol. 2389, pp. 328–339.

Graber et al, "A Perturbation Model for Imaging in Dense Scattering Media: Derivation and Evaluation of Imaging Operators", Medical Optical Tomography, pp. 121–143.

Pogue et al, "Initial Assessment of a Simple System for Frequency Domain Diffuse Optical Tomography", Phys. Med. Biol., vol. 40, 1995, pp. 1709–1729.

Colak et al, "Optical Back Projection Tomography in Heterogeneous Diffusive Media", Advances in Optical Imaging and Photon Migration, 1996, Technical.

Walker et al, "Back–Projection Image Reconstruction Using Photon Density Waves in Tissues", SPIE, vol. 2389, pp. 350–357.

Colak et al, "Optical Image Reconstruction With deConvolution in Light Diffusing Media", SPIE, vol. 2626, pp. 306–315.

Oda et al, "Optical Tomography by the Temporally Extrapolated Absorbance Method", Applied Optics, vol. 35, No. 1, Jan. 1996, pp. 169–175.

Miwa et al, "Development of Time Resolved Spectroscopy System for Quantitative Non–Invasive Tissue Measurement", SPIE, vol. 2389, pp. 142–149.

Maier et al, "Possible Correlation Between Blood Glucose Concentration and the Reduced Scattering Coeffcient of Tissues in the Near Infrared", Optics Letters.

EXAMPLE WITH UNIFORM ABSORPTION

EXAMPLE WITH DISTRIBUTION OF
ABSORPTION IN SCATTERING MEDIUM

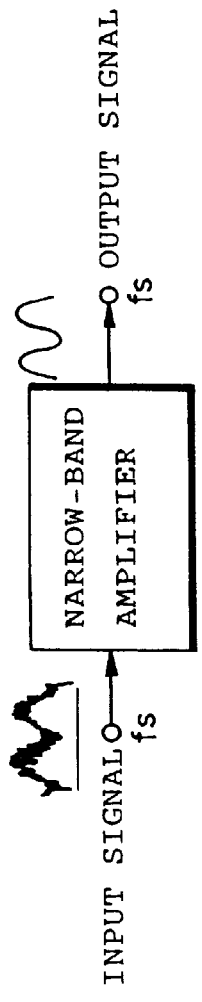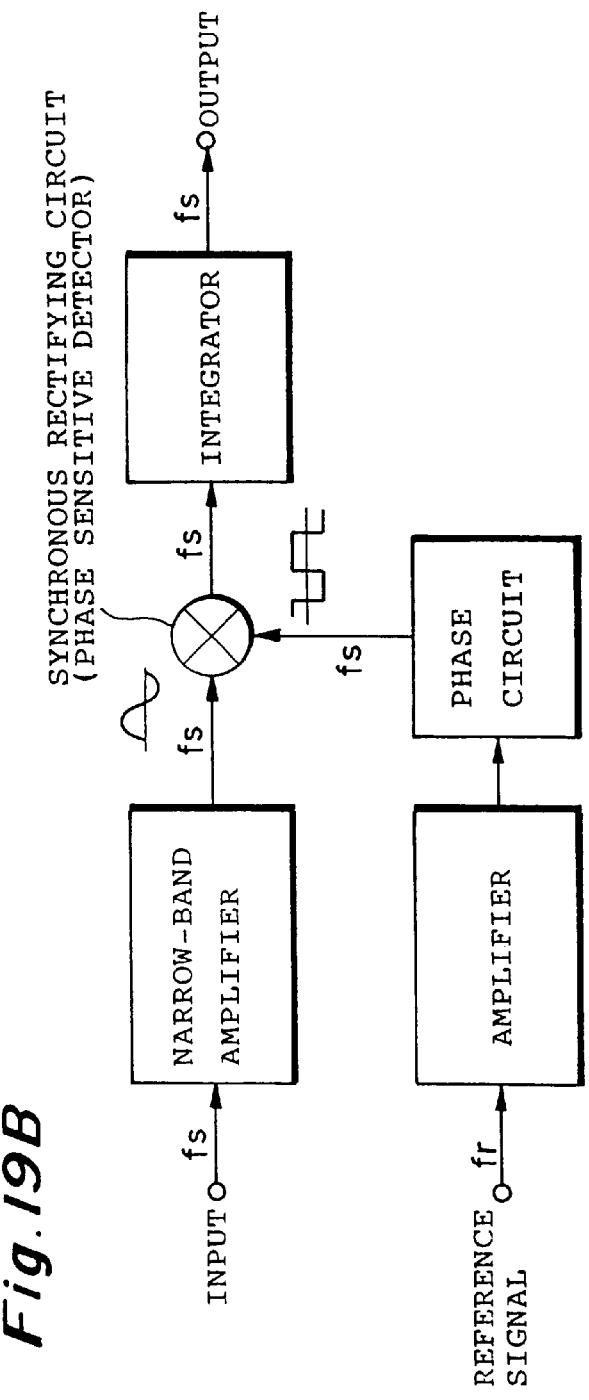

Fig. 22A
Fig. 22B
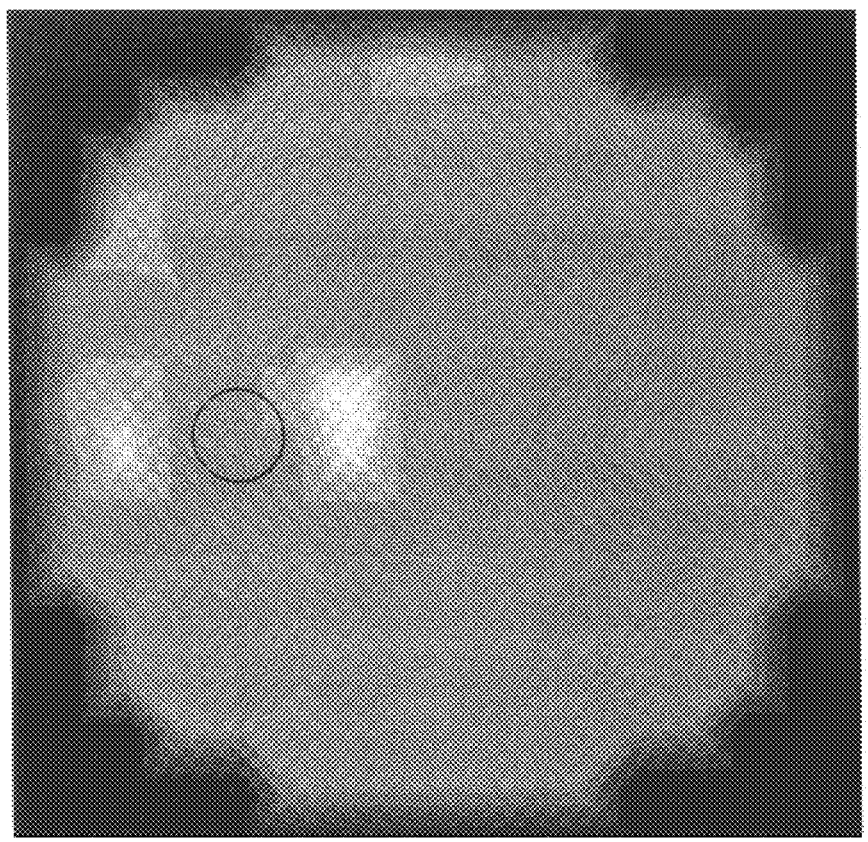
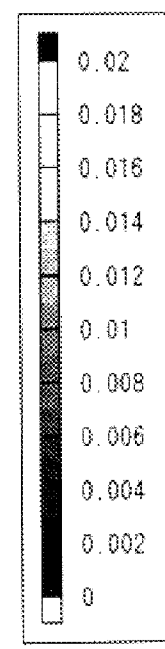

METHOD AND APPARATUS FOR MEASURING INTERNAL PROPERTY DISTRIBUTION

BACKGROUND OF THE INVENTION

1. Field of the Invention

The present invention relates to a method for measuring an internal property distribution of a measured object and an apparatus therefor. More particularly, the present invention concerns an internal property distribution measuring method and an apparatus therefor applicable to optical CT (computed tomography) apparatus or the like for obtaining a tomographic image by moving the light incidence position and light detection position along the surface of measured object.

2. Related Background Art

In the optical CT apparatus wherein measurement light is incident at one light incidence position on the surface of the object being a scattering medium, wherein the measurement light transmitted as scattered by the object is received at a plurality of light detection positions on the surface of the object, and wherein a distribution of an internal property in the scattering medium is obtained as moving the light incidence position and light detection position along the surface of the object, the following methods are known as methods for obtaining a distribution of absorption coefficient inside thereof, for example. Specifically, they are the methods described in "Imaging of Multiple Targets in Dense Scattering Media" (H. L. Graber, J. Chang, R. L. Barbour, SPIE vol. 2570, p. 219-p. 234), "Imaging diffusive media using time-independent and time-harmonic sources; dependence of image quality on imaging algorithms, target volume weight matrix, and view angles" (Jenghwa Chang et al., SPIE vol. 2389), and so on.

The basic imaging principle in such conventional methods is to use a relational equation between received light and a function indicating a contribution to the received light (which is referred to as "spread function" for convenience) where the inside of measured object is divided into a plurality of voxels for convenience, light incident from a certain point on the surface of object passes through the inside of measured object and is received at another point on the same surface, and on that occasion attention is focused on a specific internal property such as an absorption coefficient for each voxel. The voxel stated herein means each region (volume element) obtained by dividing the measured object into a plurality of regions.

In the above conventional methods, however, a phantom without absorption was prepared separately from the measured object, the quantity of detected light to be a reference was measured using it, and an aimed absorption coefficient distribution inside the scattering medium was obtained using the spread function in that state. For imaging with such methods, it was necessary to assume a phantom model (physical model) or a simulation model made so as to have a shape identical or similar to the measured object and so as to have a known internal property and to use data obtained from such a model as a reference value in calculation of imaging. Therefore, these conventional methods were not able to avoid errors caused by the difference between the actual measured object and the physical model or simulation model, individual differences of measured object, and so on, and it was very difficult to apply them, especially, to measured objects having complex structure, such as a living body.

On the other hand, a method for obtaining a spatial distribution of concentration of absorptive substance without using a phantom is the method described in the bulletin of Japanese Laid-open Patent Application No. 8-29329. The method described in the same bulletin, however, needed to use light having a plurality of wavelengths even for the cases of only one absorptive constituent in the measured object, and the spatial distribution of concentration of absorptive substance was obtained under the assumption that a mean optical pathlength distribution and attenuated light quantity (the quantity of light attenuated due to influence of scattering or the like) were constant among these wavelengths. In addition, this method assumed an imaginary subject without absorptive substance and obtained the spatial distribution of concentration of absorptive substance using the mean optical pathlength in the imaginary subject, but it did not take the change of optical pathlength due to absorption into consideration. Therefore, the method described in the above bulletin was not satisfactory yet as to reliability of internal property distribution obtained.

SUMMARY OF THE INVENTION

The present invention has been accomplished in view of the above conventional problems, and an object of the invention is to provide a method and apparatus that can obtain the reference value directly from measured values about the measured object without obtaining the reference value from the physical model or simulation model required before and without using the light having plural wavelengths for one constituent in the measured object, thus enabling to measure an internal property distribution in the measured object based on the reference value with high reliability, i.e., with high accuracy.

The present inventors conducted research eagerly to achieve the above object and found that the above problems were solved by using, as a reference value for obtaining the internal property distribution, a mean value of plural measured-values obtained by a plurality of combinations of light incidence position and light detection position located on the surface of the measured object and in the positional relation being relatively identical with respect to a point in the object (for example, the center of the object), thus coming to attain the present invention.

A measuring method of internal property distribution according to the present invention is a method comprising:

a step of making measurement light incident from a plurality of light incidence positions on a surface of a measured object successively into the object;

a step of detecting the measurement light having passed through the object successively or simultaneously at at least one light detection position out of a plurality of light detection positions on the surface of said object and in a predetermined positional relation with respect to a light incidence position at which the measurement light to be measured was incident;

a step of obtaining a measured value of a predetermined parameter of said measurement light, based on each measurement light detected at each light detection position;

a step of extracting a plurality of said measured values obtained by a plurality of combinations of said light incidence position and said light detection position said positional relation of which is relatively identical and calculating a mean value of the measured values to obtain a reference value in the positional relation; and a step of calculating a change amount of a predetermined internal property in each region of said object divided into a plurality of regions, using said plurality of measured values obtained by said plurality of combinations, and said reference value, thereby obtaining an internal property change amount distribution in the object.

A measuring apparatus of internal property distribution according to the present invention is an apparatus comprising:

light incidence means for making measurement light incident from a plurality of light incidence positions on a surface of a measured object successively into the object;

light detection means for detecting the measurement light having passed through the object successively or simultaneously at at least one light detection position out of a plurality of light detection positions on the surface of the object and in a predetermined positional relation with respect to a light incidence position at which the measurement light to be measured was incident;

measured value acquiring means for obtaining a measured value of a predetermined parameter of the measurement light, based on each measurement light detected at each light detection position;

reference value calculating means for extracting a plurality of said measured values obtained by a plurality of combinations of said light incidence position and said light detection position said positional relation of which is relatively identical and calculating a mean value of the measured values to obtain a reference value in the positional relation; and internal property change amount calculating means for calculating a change amount of a predetermined internal property in each region of said object divided into a plurality of regions, using said plurality of measured values obtained by said plurality of combinations, and said reference value, and thereby obtaining an internal property change amount distribution in the object.

In the method and apparatus of the present invention, the mean value of plural measured values obtained by the plurality of combinations of light incidence position and light detection position located on the surface of the measured object and in the positional relation relatively identical with respect to a point in the object (for example, the center of the object) is used as a reference value for obtaining the internal property distribution. Specifically, a change amount (difference) of an internal property in each region of the object divided into the plural regions is obtained by solving the equation described hereinafter, using the above reference value and each measured value.

As described, in the present invention, the reference value is obtained from the mean value of measured values obtained in actual measurement and the change amount of internal property is calculated based on this reference value. Therefore, since the present invention does not use the reference value preliminarily obtained from the physical model or simulation model, there is no room to give rise to errors caused by the individual differences of measured object, the difference of condition occurring between the actual measured object and the physical model or simulation model, and so on. Further, the present invention eliminates the work to preliminarily obtain the reference value with the physical model or the like, thus decreasing the measurement time.

"The reference value is obtained from the mean value of measured values obtained by actual measurement and a change amount of internal property or the like is obtained based on the reference value" is nothing but, for example when described with FIG. 1, "that each value of A, B, and C can be obtained if a difference from the mean value is known, without knowing the value from 0." The operation principle of the present invention is to obtain a difference or an absolute value of an internal property based on such a principle.

Since the present invention permits the internal property distribution in the measured object to be obtained without using the light having a plurality of wavelengths for one constituent in the measured object, it is free from occurrence of errors resulting from the assumption that the mean optical pathlength distribution and attenuated light quantity (the quantity of light attenuated due to influence of scattering or the like) are constant among the plurality of wavelengths, thus enhancing the measurement accuracy. Further, the present invention can also prevent occurrence of errors similarly in the case in which multiple constituents in the measured object are analyzed using the light having a plurality of wavelengths. Namely, it is because in the present invention the scattering coefficient is obtained for each wavelength in correspondence to a change of wavelength dependence of scattering coefficient which exists in real objects.

The positional relation between light incidence position and light detection position according to the present invention is defined with respect to the reference located, for example, at the center of the measured object, i.e., by an angle between a line connecting the center with the light incidence position and a line connecting the center with the light detection position, and "the positional relation is relatively identical" means, for example, that the angles defined above are identical.

The measured values according to the present invention are preferably measured values of a predetermined parameter related to scattering and absorption of the measurement light inside the measured object, and preferable measured values are those of a parameter such as the light quantity of measurement light, a phase difference (or a phase delay), the amplitude, or time-resolved waveforms.

Internal properties that can be measured by the method and apparatus of the present invention include the absorption coefficient, reduced scattering coefficient (or equivalent scattering coefficient), and refractive index, among which either one property can be obtained singly or a plurality of properties can be obtained simultaneously or successively.

First described is the case wherein the internal property to be measured by the method and apparatus of the present invention is the absorption coefficient.

In this case, the method of the present invention preferably further comprises a step of obtaining a mean absorption coefficient and a mean reduced scattering coefficient of the object (preferably, obtaining them based on said reference value), and a step of selecting a spread function (a spread function for absorption coefficient) corresponding to said mean absorption coefficient and mean reduced scattering coefficient, whereby in said step of obtaining the internal property change amount distribution the change amount of the absorption coefficient in said each region can be calculated using said plurality of measured values, said reference value, and said spread function.

Also, the apparatus of the present invention preferably further comprises mean absorption and scattering coefficient detecting means for obtaining a mean absorption coefficient and a mean reduced scattering coefficient of said object (preferably, obtaining them based on said reference value), and spread function selecting means for selecting a spread function (a spread function for absorption coefficient) corresponding to said mean absorption coefficient and mean reduced scattering coefficient, whereby in said internal property change amount calculating means the change amount of the absorption coefficient in said each region can be calculated using said plurality of measured values, said reference value, and said spread function.

By such method and apparatus of the present invention, the change amount (difference) of the absorption coefficient in said each region is obtained based on the spread function selected in correspondence to the absorption coefficient and reduced scattering coefficient as mean values measured for the measured object with nonuniform inside. Therefore, when compared with the calculation with the absorption coefficient and/or reduced scattering coefficient assumed to be zero, the method and apparatus of the present invention can fully prevent occurrence of the errors resulting from the change of effective optical pathlength caused thereby, thus enhancing the measurement accuracy.

Further, the above method of the present invention may further comprise a step of calculating an absolute value of the absorption coefficient in said each region, using said change amount of the absorption coefficient and said mean absorption coefficient, and thereby obtaining an absorption coefficient absolute value distribution in said object and/or a step of calculating a concentration of an absorptive constituent in said each region, using said absolute value of the absorption coefficient, and thereby obtaining an absorptive constituent concentration distribution in said object.

Also, the above apparatus of the present invention may further comprise absorption coefficient absolute value calculating means for calculating an absolute value of the absorption coefficient in said each region, using said change amount of the absorption coefficient and said mean absorption coefficient, and thereby obtaining an absorption coefficient absolute value distribution in said object and/or absorptive constituent concentration calculating means for calculating a concentration of the absorptive constituent in said each region, using said absolute value of the absorption coefficient, and thereby obtaining an absorptive constituent concentration distribution in said object.

By such method and apparatus of the present invention, the absolute value of absorption coefficient in each region is obtained from the change amount (difference) of absorption coefficient in said each region, based on the absorption coefficient as a mean value measured for the measured object with nonuniform inside. In this way the method and apparatus of the present invention obtain the absolute value of absorption coefficient in each region without using the reference value obtained from the phantom having the uniform absorption coefficient and the same contour as the measured object. Once the absolute value of absorption coefficient in each region is obtained, the concentration of the absorptive constituent in each region is obtained using the known molar absorption coefficient of absorptive constituent or the like. Since an error of the change amount distribution of absorption coefficient obtained by the present invention is extremely smaller than that in the case of the conventional method, the accuracy becomes high of the absolute value distribution of absorptive coefficient and the concentration distribution of absorptive constituent obtained based thereon.

When the above method of the present invention is applied to an object containing at least two absorptive constituents, the measurement light incident into said object in the light incidence step preferably has at least two wavelengths at which absorption coefficients for the absorptive constituents are different from each other. In this case, it becomes possible that in said light detection step the measurement light having said at least two wavelengths is detected respectively; that in said step of obtaining the measured values said measured values are obtained for each of said measurement light having the at least two wavelengths; that in said step of obtaining the reference value said mean value is calculated for each of said measurement light having the at least two wavelengths; that in said step of obtaining the internal property change amount distribution the change amount of said absorption coefficient is calculated for each of said measurement light having the at least two wavelengths; that in said step of obtaining the absorption coefficient absolute value distribution said absolute value of the absorption coefficient is calculated for each of said measurement light having the at least two wavelengths; and that in said step of obtaining the absorptive constituent concentration distribution said concentration of the absorptive component is calculated for each of said measurement light having the at least two wavelengths, thereby obtaining a concentration distribution of said each absorptive constituent in said object at high accuracy.

When the above apparatus of the present invention is used to measure the object containing at least two absorptive constituents, the measurement light incident into said object in said light incidence means preferably has at least two wavelengths at which absorption coefficients for the absorptive constituents are different from each other. In this case, it becomes possible that in said light detection means said measurement light having the at least two wavelengths is detected respectively; that in said measured value acquiring means said measured values are obtained for each of said measurement light having the at least two wavelengths; that in said reference value calculating means said mean value is calculated for each of said measurement light having the at least two wavelengths; that in said internal property change amount calculating means said change amount of the absorption coefficient is calculated for each of said measurement light having the at least two wavelengths; that in said absorption coefficient absolute value calculating means said absolute value of the absorption coefficient is calculated for each of said measurement light having the at least two wavelengths; and that in said absorptive constituent concentration calculating means said concentration of the absorptive constituent is calculated for each of said measurement light having the at least two wavelengths, thereby obtaining a concentration distribution of said each absorptive constituent in said object at high accuracy.

Next described is the case wherein the internal property to be measured by the method and apparatus of the present invention is the reduced scattering coefficient.

In this case, the method of the present invention preferably further comprises a step of obtaining a mean absorption coefficient and a mean reduced scattering coefficient of said object (preferably, obtaining them based on said reference value); and a step of selecting a spread function (a spread function for reduced scattering coefficient) corresponding to said mean absorption coefficient and mean reduced scattering coefficient, whereby in said step of obtaining the internal property change amount distribution, a change amount of the reduced scattering coefficient in said each region can be calculated using said plurality of measured values, said reference value, and said spread function.

Also, the apparatus of the present invention preferably further comprises mean absorption and scattering coefficient detecting means for obtaining a mean absorption coefficient and a mean reduced scattering coefficient of said object (preferably, obtaining them based on said reference value);

and spread function selecting means for selecting a spread function (a spread function for reduced scattering coefficient) corresponding to said mean absorption coefficient and mean reduced scattering coefficient; whereby in said internal property change amount calculating means, a change amount of the absorption coefficient in said each region can be calculated using said plurality of measured values, said reference value, and said spread function.

By such method and apparatus of the present invention, the change amount (difference) of reduced scattering coefficient in said each region is obtained based on the spread function selected in correspondence to the absorption coefficient and reduced scattering coefficient as mean values measured for the measured object with nonuniform inside. Accordingly, when compared with the case of calculation based on the assumption that the absorption coefficient and/or reduced scattering coefficient is zero, the method and apparatus of the present invention can fully prevent occurrence of the errors based on the change of effective optical pathlength caused thereby, thus enhancing the measurement accuracy.

Further, the above method of the present invention may further comprise a step of calculating an absolute value of the reduced scattering coefficient in said each region, using the change amount of said reduced scattering coefficient and said mean reduced scattering coefficient, and thereby obtaining a reduced scattering coefficient absolute value distribution in said object.

Also, the above apparatus of the present invention may further comprise absorption coefficient absolute value calculating means for calculating an absolute value of the absorption coefficient in said each region, using said change amount of the absorption coefficient and said mean absorption coefficient, and thereby obtaining an absorption coefficient absolute value distribution in said object.

By such method and apparatus of the present invention, the absolute value of reduced scattering coefficient in each region is obtained from the change amount (difference) of reduced scattering coefficient in said each region, based on the reduced scattering coefficient as a mean value measured for the measured object with nonuniform inside. In this way the method and apparatus of the present invention obtain the absolute value of reduced scattering coefficient in each region without using the reference value obtained from the phantom having the uniform reduced scattering coefficient and having the same contour as the measured object. When compared with the case by the conventional methods, the error of change amount distribution of reduced scattering coefficient obtained by the present invention becomes extremely smaller, thus enhancing the accuracy of absolute value distribution of reduced scattering coefficient obtained based thereon.

Next described is the case wherein the internal property to be measured by the method and apparatus of the present invention is the refractive index.

In this case the method of the present invention preferably further comprises a step of obtaining a mean absorption coefficient, a mean reduced scattering coefficient, and a mean refractive index of said object (preferably, obtaining them based on said reference value); and a step of selecting a spread function (a spread function for refractive index) corresponding to said mean absorption coefficient, mean reduced scattering coefficient, and mean refractive index; whereby in said step of obtaining the internal property change amount distribution, a change amount of the refractive index in said each region can be calculated using said plurality of measured values, said reference value, and said spread function.

Also, the apparatus of the present invention preferably further comprises mean absorption and scattering coefficient detecting means for obtaining a mean absorption coefficient, a mean reduced scattering coefficient, and a mean refractive index of said object (preferably, obtaining them based on said reference value); and spread function selecting means for selecting a spread function (a spread function for refractive index) corresponding to said mean absorption coefficient, mean reduced scattering coefficient, and mean refractive index; whereby in said internal property change amount calculating means, a change amount of the refractive index in said each region can be calculated using said plurality of measured values, said reference value, and said spread function.

By such method and apparatus of the present invention, the change amount (difference) of refractive index in said each region is obtained based on the spread function selected in correspondence with the absorption coefficient, reduced scattering coefficient, and refractive index as mean values measured for the measured object with nonuniform inside. Accordingly, as compared with the case of calculation under the assumption that the absorption coefficient and/or reduced scattering coefficient is zero, such method and apparatus of the present invention can fully prevent occurrence of the errors based on the change of effective optical pathlength caused thereby, thus enhancing the measurement accuracy.

Further, the above method of the present invention may further comprise a step of calculating an absolute value of the refractive index in said each region, using said change amount of the refractive index and said mean refractive index, and thereby obtaining a refractive index absolute value distribution in said object.

Also, the above apparatus of the present invention may further comprise refractive index absolute value calculating means for calculating an absolute value of the refractive index in said each region, using said change amount of the refractive index and said mean refractive index, and thereby obtaining a refractive index absolute value distribution in said object.

By such method and apparatus of the present invention, the absolute value of refractive index in each region is obtained from the change amount (difference) of refractive index in said each region, based on the refractive index as a mean value measured for the measured object with nonuniform inside. In this way the method and apparatus of the present invention obtain the absolute value of refractive index in each region without using the reference value obtained from the phantom having the uniform refractive index and having the same contour as the measured object. The error of change amount distribution of refractive index obtained by the present invention becomes extremely smaller than that in the case by the conventional methods, thereby enhancing the accuracy of absolute value distribution of refractive index obtained based thereon.

The above-stated method of the present invention may further comprise a step of displaying an image indicating the distribution inside said object, based on said distribution obtained. Also, the above-stated apparatus of the present invention may further comprise image display means for displaying an image indicating the distribution inside said object, based on said distribution obtained. Such method and apparatus of the present invention can display the image of the internal property distribution obtained at high accuracy.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIGS. 19A and 19B are schematic drawings each to show an example of the low-noise amplifying method of detection signal.

FIGS. 22A and 22B are photographs to show a half-tone image displayed on the display as a result of reconstruction of image by the conventional method.

DESCRIPTION OF THE PREFERRED EMBODIMENTS

Figure 1:
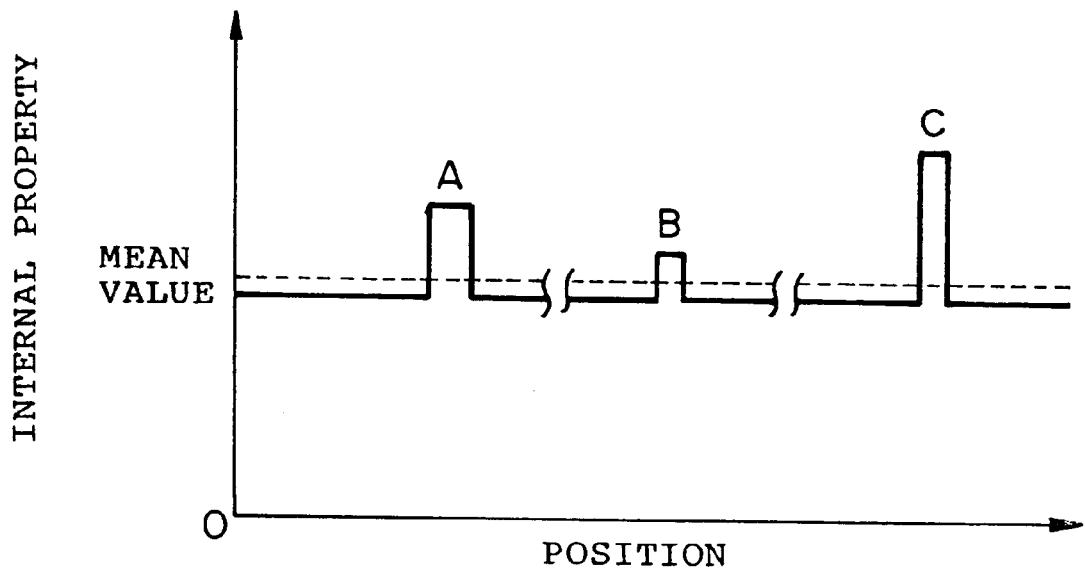
FIG. 1 is an explanatory drawing of the operation principle of the present invention.

The preferred embodiments of the present invention will be described in detail with reference to the drawings. In the drawings identical or equivalent portions will be denoted by same reference numerals.

Figure 2:
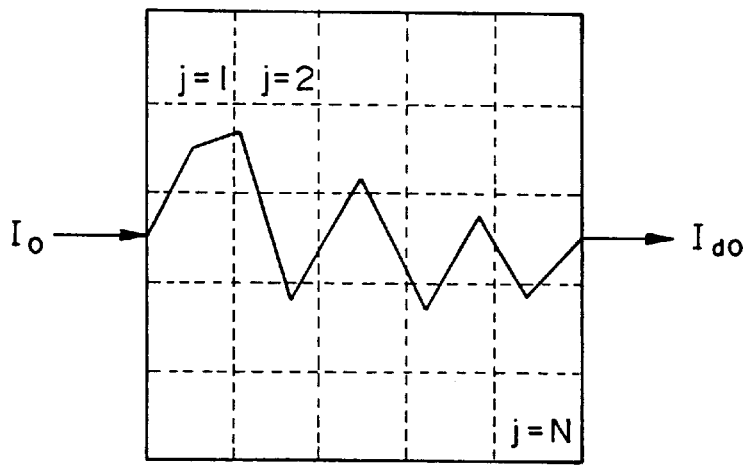
FIG. 2 is a schematic drawing to show a model of the scattering medium with uniform absorption.
Figure 3:
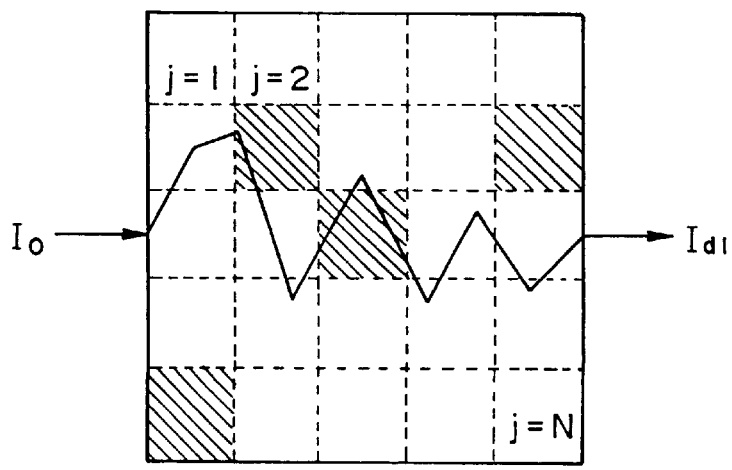
FIG. 3 is a schematic drawing to show a model of the scattering medium with nonuniform absorption.

The imaging principle of light CT used in the present embodiment will be first described referring to FIG. 2 and FIG. 3. It is necessary to handle light propagating as scattered with 3-dimensional coordinates, but the following discussion employs 2-dimensional coordinates for simplifying the description.

First, let us divide the inside of a scattering medium into N voxels and consider the relation between quantity of incident light and quantity of emergent light (quantity of detected light) with respect to the scattering medium under a condition that the absorption coefficient exists. FIG. 2 shows a schematic diagram of the inside of the scattering medium with uniform reduced scattering coefficient $\mu'_s$ and absorption coefficient $\mu_a$ (N=25). Equation (1) below holds, where $I_0$ is the quantity of incident light, $I_{d0}$ the quantity of detected light, $W_1$ an effective optical pathlength in each voxel when the reduced scattering coefficient $\mu'_s$ its and absorption coefficient $\mu_a$ inside the scattering medium are uniform, and $D_{sr}$ a damping factor to indicate a rate of outgoing light from the scattering medium to the incident light because of scattering and reflection or the like.

$$I_{d0} = D_{sr} \cdot I_0 \cdot \exp\{-\mu_a(W_1 + W_2 + \cdots + W_N)\} \quad (1)$$

Next, FIG. 3 shows a schematic diagram of the inside of another scattering medium that is the same as the one shown in FIG. 2 except that a medium having the same reduced scattering coefficient but a different absorption coefficient is put in some voxels. The relation between absorption coefficient $\mu_{ai}$ (i=1, 2, ..., N) of each medium used in the scattering medium shown in FIG. 3 and absorption coefficient $\mu_a$ of the medium used in the scattering medium shown in FIG. 2 is the relation as shown in Eq. (2) below.

$$\mu_{a_i} = \mu_a + \Delta \mu_{a_i} \; (i=1, 2, \cdots N) \quad (2)$$

Letting $I_0$ be the quantity of incident light at this time and $I_{d1}$ be the quantity of detected light and supposing that the damping factor $D_{sr}$ to indicate the rate of outgoing light from the scattering medium to the incident light because of scattering and reflection or the like is equal to that when the absorption coefficient was uniform (FIG. 2), the quantity of detected light $I_{d1}$ can be expressed by Eq. (3) below.

$$I_{d1} = D_{sr} \cdot I_0 \cdot \exp\{-[W_1(\mu_a + \Delta_{a_1}) + W_2(\mu_a + \Delta \mu_{a_2}) + \cdots + W_N(\mu_a + \Delta \mu_{a_N})]\} = I_{d0} \cdot \exp\{-(W_1 \Delta \mu_{a_1} + W_2 \Delta \mu_{a_2} + \cdots + W_N \Delta \mu_{a_N})\} \quad (3)$$

Accordingly, Eq. (4) below is derived from Eq. (3).

$$\ln I_{d0} - \ln I_{d1} = (W_1 \Delta \mu_{a_1} + W_2 \Delta \mu_{a_2} + \cdots + W_N \Delta \mu_{a_N}) \quad (4)$$

-continued $$= \sum_{j=1}^{N} W_j \Delta \mu_{a_j}$$

In this way, use of reference light quantity $I_{d0}$ permits a distribution of absorption coefficient $\mu_a$ inside the scattering medium to be obtained from the relation between the absorption coefficient $\mu_a$ desired to obtain and the detected light quantity $I_{d1}$ that can be measured by an actual experiment system when the effective optical pathlength $W_j$ is determined. Eq. (4) indicates the relation that holds for a pair of light incidence position and light detection position. Accordingly, for example, for obtaining N absorption coefficients (unknowns), N combinations of light incidence position and light detection position are selected and simultaneous equations of N Eqs. (4) holding for the respective combinations are solved, thus obtaining the N absorption coefficients.

Namely, when the simultaneous equations of N Eqs. (4) that hold for the N combinations of light incidence position and light detection position are expressed in the form of matrix representation, Eq. (5) below is yielded.

$$[\Delta I]=[W][\Delta \mu_a] \qquad (5)$$

Here, $\Delta I$ represents ($\ln I_{d0} - \ln I_{d1}$) and W represents a spread function to indicate a distribution of effective optical pathlength of each voxel. Letting X be the number of light incidence positions M ($M_1$ to $M_x$), x be the number of light detection positions m ($m_1$ to $m_x$), $\Delta I_{Mm}$ be a change amount in the light quantity in the case of the light incidence position M and light detection position m, and $W_{Mm}$ be a spread function of each voxel in the case of the light incidence position M and light detection position m, $[\Delta I_{Mm}]$ is a matrix of $(X^*x)^*1$, $[W_{Mm}]$ a matrix of $(X^*x)^*N$, and $[\Delta \mu_{a_n}]$ a matrix of $N^*1$. Therefore, change amounts $\Delta \mu_{a_n}$ of absorption coefficient can be obtained by solving the simultaneous equations of Eq. (6) below. The simultaneous equations of Eq. (6) are preferably to be solved by selecting such values of X and x as to satisfy $X^*x=N$.

$$[\Delta \mu_{a_n}]=[W_{Mm}]^{-1}[\Delta I_{Mm}] \qquad (6)$$

For quantifying the absorption coefficients inside the scattering medium by such an image reconstructing method, the state to be a reference as shown in FIG. 2 is basically necessary, and in the above case the absorption coefficient of each voxel was obtained from Eq. (2) and Eq. (4), because the uniform state of absorption coefficient was assumed to be the reference. However, such an imaging method requires only preliminarily knowing the value of internal absorption coefficient and the light quantity at each light detection position at that time, but does not force any specific restriction on the state of reference to be used actually. Specifically, for example, when an internal absorption coefficient is obtained with the reference at the value of internal absorption coefficient under a certain condition and the light quantity at each light detection position at that time, a value of the absorption coefficient is obtained in the form of a difference from the value of reference.

Conventionally, such value of internal absorption coefficient and light quantity at each light detection position at that time, to be the reference, were obtained from a phantom model or a simulation model different only in internal absorption coefficient from the scattering medium as a measured object.

However, the present invention employs a mean value of plural measured values obtained with a plurality of combinations of light incidence position and light detection position located on the surface of the measured object and in the relatively same positional relation with respect to a point in the object (the center of the object, for example), as a reference value for obtaining an internal property distribution. A method for producing the effective optical pathlength of each voxel is described in Japanese Patent Application No. 8-6619 of the present inventors entitled "Optical CT apparatus and image reconstructing method by optical CT" etc. In the present embodiment, according to this producing method, a distribution of effective optical pathlength (i.e., a spread function) of each voxel in certain relation of light incidence position and light detection position is preliminarily prepared based on a mean value of absorption coefficient, a mean value of reduced scattering coefficient, and the like. In this way, the present embodiment permits the reference value to be obtained directly from measured values about the measured object without obtaining the reference value from the physical model or simulation model conventionally required and permits the distribution of internal property of the measured object to be measured at high accuracy based on the reference value.

The foregoing described the embodiment using CW measurement, but it is also possible to apply time-resolved measurement in the present invention. Specifically, Eq. (3) described above expresses the detected light as an integral value of detected light quantity received by the detector between times 0 and t (s), but the same relational expression also holds in the case of time-resolved waveforms obtained by the detector when a light source is of pulsed light. Rewriting Eq. (3) with respect to a certain time period $t_1$ to $t_2$, Eq. (7) below is obtained.

$$[I_{d1}]_{t_1-t_2}=[I_{d0}]_{t_1-t_2}\exp\{-([W_1]_{t_1-t_2}\Delta\mu_{a_1}+[W_2]_{t_1-t_2}\Delta\mu_{a_2}+\cdots+[W_N]_{t_1-t_2}\Delta\mu_{a_N})\} \qquad (7)$$

Here, $[I_{d0}]_{t1-t2}$, $[I_{d1}]_{t1-t2}$ represent light quantities of time-resolved waveforms of each detected light between times $t_1$ and $t_2$, and $[W_j]_{t1-t2}$ represents the spread function between times $t_1$ and $t_2$ (where j indicates a number of each voxel). Also, $0 \le t_1 \le t_2$. Therefore, Eq. (8) below is derived from Eq. (7).

$$\ln[I_{d0}]_{t_1-t_2} - \ln[I_{d1}]_{t_1-t_2} = ([W_1]_{t_1-t_2}\Delta\mu_{a_1} + \qquad (8)$$
$$[W_2]_{t_1-t_2}\Delta\mu_{a_2} + \cdots +$$
$$[W_N]_{t_1-t_2}\Delta\mu_{a_N})$$
$$= \sum_{j=1}^{N}[W_j]_{t_1-t_2}\Delta\mu_{a_j}$$

As described, the method using the time-resolved measurement permits an absorption coefficient of each voxel to be obtained by increasing the number of equations with various sections of measurement periods and solving N equations numbering in the same as the number of voxels.

The above embodiment was described with the internal property to be measured being the absorption coefficient, but the present invention can be applied to other internal properties including the reduced scattering coefficient (or equivalent scattering coefficient) and index of refraction. Specifically, the light received after passed through the inside of object is affected not only by the absorption coefficient and reduced scattering coefficient which the inside of the object has, but also by the all internal properties which the object has, and they act on the received light linearly and independently. For obtaining internal properties affecting each other, independence can be assured by regarding them as one internal property.

From these relations, values of the all internal properties which the object has are expressed by equations using the received light and functions to indicate contributions of the internal properties in each voxel to the received light (the spread functions), and use of these permits the distribution of reduced scattering coefficient or absorption coefficient to be obtained as described, for example, in "Forward and Inverse Calculations for 3-D Frequency-Domain Diffuse Optical Tomography" (Brian W. Pogue et al., SPIE vol. 2389, p. 328-p. 338). In such cases, the method of the present invention can also be applied as a deriving method of the reference value of a parameter such as the amplitude or the phase of detected light. Accordingly, when the reference value deriving method according to the present invention is applied to the relational expression using the received light and the functions to indicate contributions to the received light (the spread functions) and, for the internal properties such as the absorption coefficient, the reduced scattering coefficient, and the refractive index, quantification of these internal properties becomes possible. Examples of such relational expressions include the below equations. Namely, equations applicable to acquisition of absorption coefficient and reduced scattering coefficient are Eq. (4') and Eq. (8') below, which are modifications of above Eq. (4) and Eq. (8).

$$\ln I_{d0} - \ln I_{dI} = (W_{\mu_a,1}\Delta\mu_{a1} + W_{\mu'_s,1}\Delta\mu'_{s1} + W_{\mu_a,2}\Delta\mu_{a2} + \quad (4')$$
$$W_{\mu'_s,2}\Delta\mu'_{s2} + \cdots +$$
$$W_{\mu_a,N}\Delta\mu_{aN} + W_{\mu'_s,N}\Delta\mu'_{sN})$$
$$= \sum_{j}^{N}(W_{\mu_a,j}\Delta\mu_{aj} + W_{\mu'_s,j}\Delta\mu'_{sj})$$

$$\ln[I_{d0}]_{t_1-t_2} - \ln[I_{dI}]_{t_1-t_2} = ([W_{\mu_a,1}]_{t_1-t_2}\Delta\mu_{a1} + \quad (8')$$
$$[W_{\mu'_s,1}]_{t_1-t_2}\Delta\mu'_{s1} + \cdots +$$
$$[W_{\mu_a,N}]_{t_1-t_2}\Delta\mu_{aN} +$$
$$[W_{\mu'_s,N}]_{t_1-t_2}\Delta\mu'_{sN})$$
$$= \sum_{j=1}^{N}([W_{\mu_a,j}]_{t_1-t_2}\Delta\mu_{aj} +$$
$$[W_{\mu'_s,j}]_{t_1-t_2}\Delta\mu'_{sj})$$

Further, equations applicable to acquisition of absorption coefficient, reduced scattering coefficient, and refractive index are Eq. (4") and Eq. (8") below, which are modifications of above Eq. (4) and Eq. (8).

$$\ln I_{d0} - \ln I_{dI} = (W_{\mu_a,1}\Delta\mu_{a1} + W_{\mu'_s,1}\Delta\mu'_{s1} + W_{n,1}\Delta n_1 + \cdots + \quad (4")$$
$$W_{\mu_a,N}\Delta\mu_{aN} + W_{\mu'_s,N}\Delta\mu'_{sN} + W_{n,N}\Delta n_j)$$
$$= \sum_{j}^{N}(W_{\mu_a,j}\Delta\mu_{aj} + W_{\mu'_s,j}\Delta\mu'_{sj} + W_{n,j}\Delta n_N)$$

$$\ln[I_{d0}]_{t_1-t_2} - \ln[I_{dI}]_{t_1-t_2} = ([W_{\mu_a,1}]_{t_1-t_2}\Delta\mu_{a1} + \quad (8")$$
$$[W_{\mu'_s,1}]_{t_1-t_2}\Delta\mu'_{s1} +$$
$$[W_{n,1}]_{t_1-t_2}\Delta n_1 + \cdots +$$
$$[W_{\mu_a,N}]_{t_1-t_2}\Delta\mu_{aN} +$$
$$[W_{\mu'_s,N}]_{t_1-t_2}\Delta\mu'_{sN} +$$
$$[W_{n,N}]_{t_1-t_2}\Delta n_N)$$
$$= \sum_{j=1}^{N}([W_{\mu_a,j}]_{t_1-t_2}\Delta\mu_{aj} +$$
$$[W_{\mu'_s,j}]_{t_1-t_2}\Delta\mu'_{sj} +$$
$$[W_{n,j}]_{t_1-t_2}\Delta n_j)$$

Even in the case of one internal property being obtained, the measurement accuracy tends to be enhanced with use of spread functions corresponding to all internal properties affecting the detected light. Accordingly, when the measured object has the absorption coefficient, reduced scattering coefficient, refractive index, and so on as internal properties like a living body, there are some cases wherein use of at least the spread functions corresponding to the mean value of absorption coefficient and the mean value of reduced scattering coefficient (in the case of time-resolved measurement being carried out, the mean value of absorption coefficient, the mean value of reduced scattering coefficient, and the mean value of refractive index) is preferable even in the case of imaging only the distribution of absorption coefficient.

Figure 4:
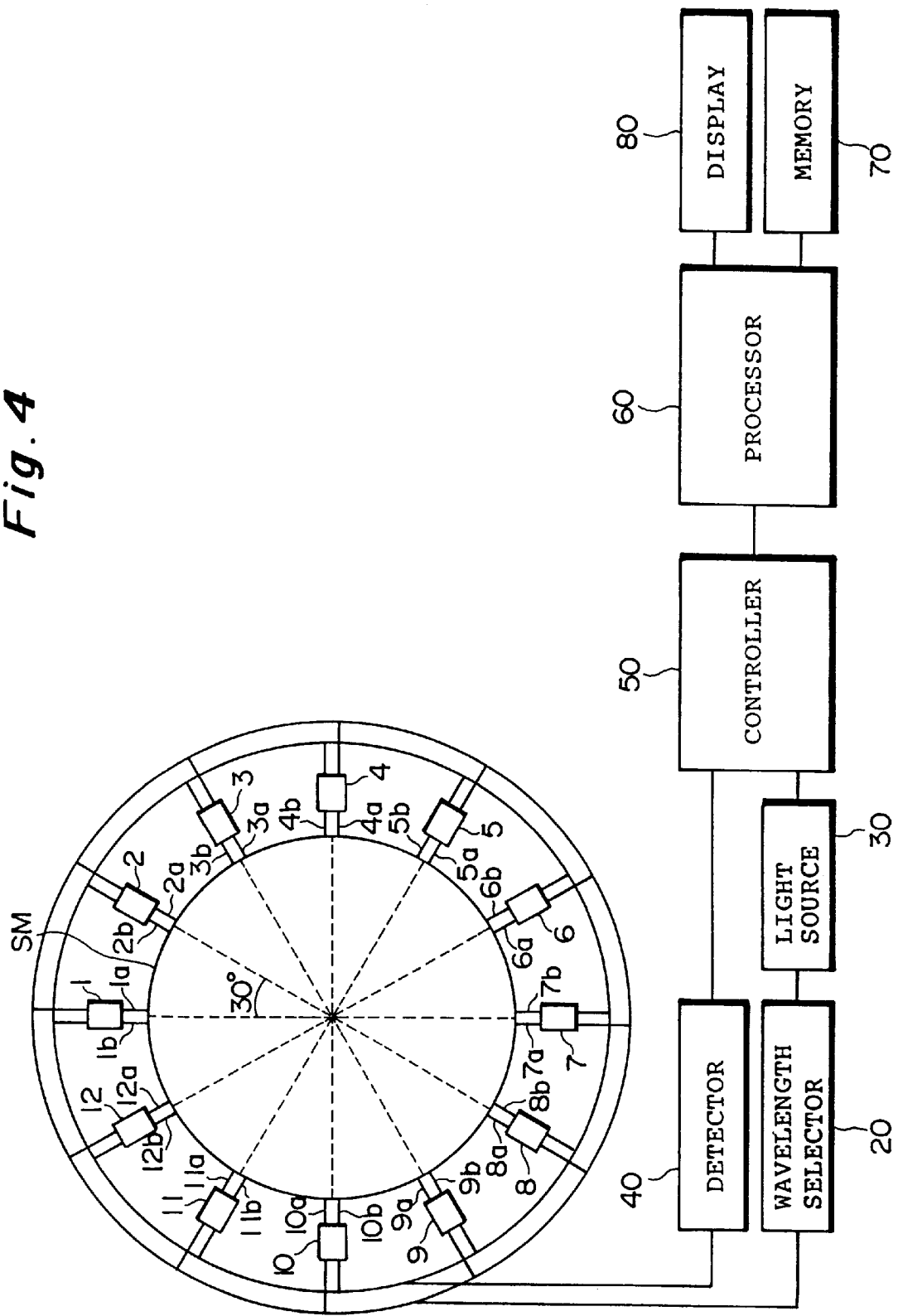
FIG. 4 is a schematic drawing to show an example of the internal property distribution measuring apparatus of the present invention.

Next described is an internal property distribution measuring apparatus of the present invention. FIG. 4 shows a schematic diagram of an embodiment of the apparatus of the present invention.

The apparatus shown in FIG. 4 is provided with twelve fiber-optic holders 1 to 12 (which will also be referred totally as an "optical fiber holder group", if necessary), and the fiber-optic holders 1 to 12 are arranged at equal intervals around a cross section of scattering medium SM (in the apparatus shown in FIG. 4, they are placed on lines each extending radially at intervals of 30 degrees from the center of scattering medium SM) and are denoted by numbers of 1 to 12 in the clockwise direction.

Figure 5A:
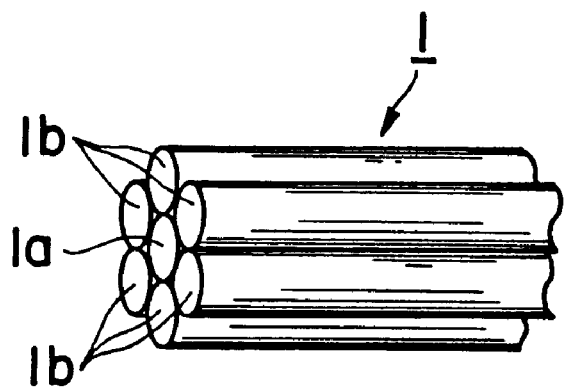
FIGS. 5A and 5B are a perspective view and a schematic view, respectively, to show an example of the light incidence fiber.
Figure 5B:
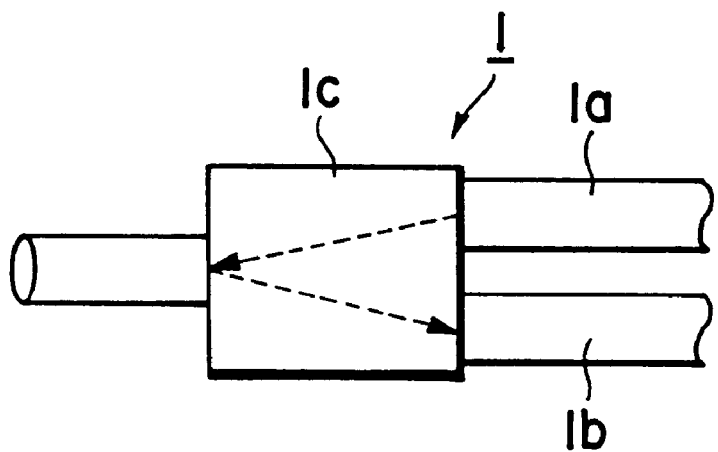

Each fiber-optic holder 1 to 12 has a light incidence fiber 1a to 12a and a light detection fiber 1b to 12b. The light incidence fiber 1a to 12a and light detection fiber 1b to 12b may be constructed in such structure that they are bundled in parallel as shown in FIG. 4, but they may also be formed in such bundled structure that a plurality of light detection fibers 1b (bundle fibers) surround a light incidence fiber 1a as shown in FIG. 5A or in such structure that a light incidence fiber 1a and a light detection fiber 1b are coupled by an optical coupler 1c in the fiber-optic holder as shown in FIG. 5B. Employment of the structures as shown in FIG. 5A and FIG. 5B will result in a tendency to reduce errors, because only one fiber end face is in contact with the periphery of scattering medium SM whereby positional deviation can be suppressed between the end of light incidence fiber and the end of light detection fiber, as compared with the cases wherein the two fibers are arranged vertically in two steps or horizontally in two columns.

A light source 30 is optically connected through wavelength selector 20 to the light incidence fibers 1a to 12a. Then, light emitted from the light source 30 is subjected to wavelength selection in the wavelength selector 20 to be incident through the optical fiber holder 1 to 12 to the surface of scattering medium SM being a measured object. The light source 30 may be selected from various sources including light emitting diodes, laser diodes, He-Ne laser, and so on. The light source 30 may be one for generating pulsed light or rectangular-wave light, or modulated light thereof.

Figure 6:
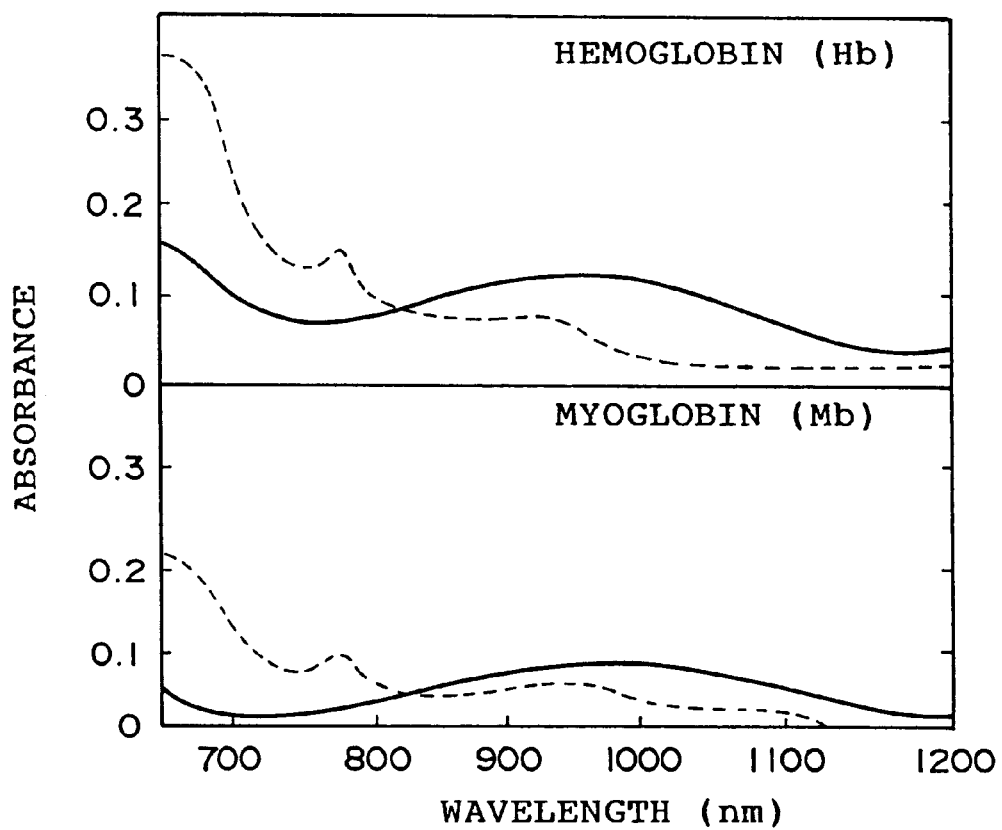
FIG. 6 is a graph to show absorption spectra of hemoglobin and myoglobin.

The light source 30 used in the present embodiment may be one for emitting light (measured light) of a single wavelength, but it is preferably one capable of emitting light (measured light) of two or more wavelengths. The wavelength of the light used for measurement is properly selected depending upon a measured object. In general, in the case of living bodies, it is preferable to use light of 700 or more nm from absorption characteristics of hemoglobin or the like, particularly preferably, the visible light or near infrared light. For example, when the object is oxygenated hemoglobin and deoxygenated hemoglobin, because their absorption coefficients are different from each other as shown in FIG. 6, use of properly selected wavelength permits them to be measured as separating them.

A detector 40 is optically connected to the light detection fibers 1b to 12b. Then, light (measurement light) transmitted as scattered in the scattering medium SM is guided through the light detection fiber 1b to 12b of fiber-optic holder 1 to 12 to the detector 40 and the photodetector 40 converts a signal of received light to an amplified detection signal (electric signal) and outputs the detection signal corresponding to each fiber. The photodetector 40 may be selected from all types of photodetectors including photomultiplier tubes, phototubes, photodiodes, avalanche photodiodes, PIN photodiodes, and so on. The point in selection of photodetector 40 is that the detector has spectral sensitivity characteristics capable of detecting light of the wavelength of the measurement light used. When light signals are weak, it is preferable to use a photodetector with high sensitivity or high gain. It is desirable to make the other places than light receiving surfaces of light detection fibers 1b to 12b and photodetector 40 in the structure to absorb or shield light. In the case wherein the light having propagated diffusely inside the scattering medium SM includes light of plural wavelengths, a wavelength selection filter (not illustrated) may be placed, if necessary, between the photodetector 40 and the scattering medium SM.

A control unit 50 is connected to the light source and to the detector 40 and selection of fiber-optic holder 1 to 12 used in incidence or acceptance is carried out by the control unit 50. Namely, the control unit 50 performs such control that the measurement light is incident into the scattering medium SM at constant time intervals successively (for example, $1a \rightarrow 2a \rightarrow 3a \rightarrow \ldots \rightarrow 12a$) from the light incidence fibers and such control that in synchronism therewith the measurement light is detected from the light detection fibers located in the predetermined positional relation with respect to the light incidence fibers through which the measurement light was incident. In the present embodiment, the measurement light is detected from each of the all light detection fibers at different locations from the light incidence fiber through which the measurement light was incident (for example, from the light detection fibers 2b to 12b in the case of the light incidence fiber being 1a), but the combination does not have to be limited particularly to such a combination.

Figure 7A:
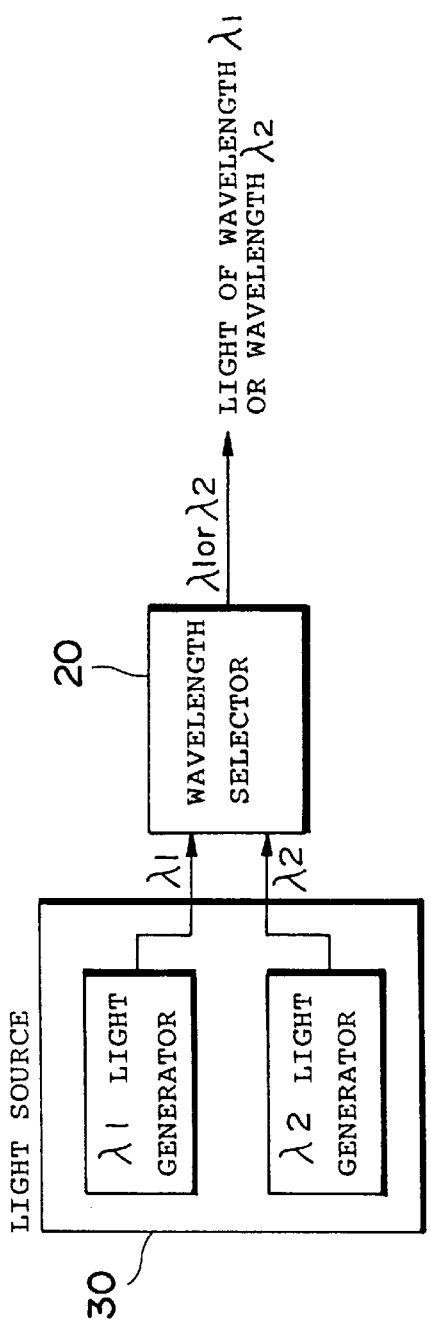
FIGS. 7A and 7B are schematic drawings to show an example of the light incidence means.

When the measurement light having a plurality of wavelengths is used, a wavelength of the measurement light to be launched is also controlled by the control unit 50. Specific techniques include a technique for using light of different wavelengths as launched in time division and a technique for using light simultaneously including light components of different wavelengths as described below. Specific wavelength selecting means include a light beam switching device using a mirror, a wavelength switching device using a filter, a light switching device using an optical switch, and so on (FIG. 7A).

The above light incidence fibers 1a to 12a, wavelength selector 20, light source 30, and control unit 50 compose light incidence means according to the present invention, while the above light detection fibers 1b to 12b, detector 40, and control unit 50 compose light detection means according to the present invention.

A processing unit (for example, CPU) 60 is electrically connected to the control unit 50, and a memory unit (for example, a hard disk or a flexible disk) 70 and a display unit (for example, a display or a printer) 80 are electrically connected to the processing unit 60. A detection signal output from the detector 40 is guided through the control unit 50 to the processing unit 60.

The above processing unit 60 and memory unit 70 compose measured value acquiring means, reference value calculating means, internal property change amount calculating means, mean absorption and scattering coefficient detecting means, spread function selecting means, absorption coefficient absolute value calculating means, absorptive constituent concentration calculating means, reduced scattering coefficient absolute value calculating means, and refractive index absolute value calculating means according to the present invention, while the above display unit 80 composes image display means. Such means according to the present invention will be described in detail based on the flowchart of an embodiment of the method of the present invention shown in FIG. 8.

(1) In the method shown in FIG. 8, first, measurement data ($I_{d1}\{M, m\}$) by optical CT is acquired as described below (S100). Here, M represents a number of light incident fiber and m a number of light detection fiber.

Specifically, the measurement light is incident from the light incidence fibers 1a to 12a successively into the scattering medium SM, and each measurement light having transmitted as scattered in the scattering medium SM is detected successively or simultaneously from the all light detection fibers located at different locations from the light incidence fiber through which the measurement light was incident (for example, from the light detection fibers 2b to 12b in the case of the light incidence fiber being 1a). For simultaneously detecting the respective measurement light beams, photodetectors 40 need to be prepared in the number corresponding to the number of light detection fibers.

Then, the photodetector 40 outputs a detection signal based on each measurement light detected through each light detection fiber. Then, each of these detection signals is processed in the processing unit 60 to be converted into a measured value proportional to each detected light quantity of the measurement light detected, and measured values obtained are stored temporarily in the memory unit 70. Specifically, the processing unit 60 performs an integration arithmetic in a time domain for the detection signals, utilizing a signal synchronous with generation of light from the light source 30, and thus obtains measured values proportional to quantities of detected light. However, the synchronous signal can be omitted if pulsed light or the like is utilized. The arithmetic process of this type can be executed at high speed by a microcomputer or the like incorporated in the processing means. Also, the processing unit 60 may be arranged to correct the measured values utilizing averaging filtering, least square fitting or the like.

2) Next, the processing unit 60 extracts a plurality of measured values obtained by plural combinations of light incidence fibers with light detection fibers the positional relation of which is relatively identical, and calculates a reference value ($I_{d0}\{M, m\}$) being a mean value of those measured values (S110).

Namely, in order to obtain the reference value for gaining a change amount in the absorption coefficient or the like, the processing unit 60 obtains the mean value of measured values for every pair of light incidence and light detection positions the positional relation of light incidence and light detection of which is relatively identical.

Specifically describing it based on FIG. 4, for example, in the case of the positional relation wherein an angle made by the light incidence fiber, the center of scattering medium SM, and the light detection fiber is 180 degrees, combinations of light incidence-light detection positions being relatively identical are (1, 7), (2, 8), (3, 9), (4, 10), (5, 11), and (6, 12), when expressed by (number of light incidence holder, number of light detection holder). When the reciprocity theorem of light does not hold, it is necessary to take the opposite combinations of light incidence and light detection positions into consideration.

When the respective measured values are I(1, 7), I(2, 8), I(3, 9), I(4, 10), I(5, 11), and I(6, 12), the mean value of these is given by the following equation.

$$I(ave\_180)=\{I(1, 7)+I(2, 8)+I(3, 9)+I(4, 10)+I(5, 11)+I(6, 12)\}/6$$

This I(ave__180) is defined as a reference value when the positional relation of light incidence-light detection is 180 degrees.

Similarly, I(ave__150), I(ave__120), I(ave__90), I(ave__60), and I(ave__30) are also obtained and these mean values are stored as reference values in the above respective positional relations temporarily in the memory unit 70.

3) Next, in the present embodiment, mean absorption coefficient $\mu_{a0}$ and mean reduced scattering coefficient $\mu'_{s0}$ can be obtained utilizing the photon diffusion theory or the like, based on the reference values in the above respective positional relations and the like (S120).

Specifically, internal absorption coefficients and reduced scattering coefficients are obtained from the reference values of every angle, mean values thereof are further calculated, and they are temporarily stored as mean absorption coefficient $\mu_{a0}$ and mean reduced scattering coefficient $\mu'_{s0}$ inside the scattering medium, in the memory unit 70. There occurs no inconvenience when the mean absorption coefficient $\mu_{a0}$ and mean reduced scattering coefficient $\mu'_{s0}$ inside the scattering medium SM are obtained from only the reference value of either one angle, for example, from only the value of I(ave__180).

A method for obtaining the absorption coefficients and reduced scattering coefficients inside the scattering medium SM from the above reference values is, for example, the method described in "Imaging diffusive media using time-independent and time-harmonic sources; dependence of image quality on imaging algorithms, target volume weight matrix, and view angles" (Jenghwa Chang et. al., SPIE vol. 2389).

4) Next, in the present embodiment, a spread function (Wθ) corresponding to the above mean absorption coefficient $\mu_{a0}$ and mean reduced scattering coefficient $\mu'_{s0}$ is selected (S130).

Namely, a spread function matching with the mean absorption coefficient $\mu_{a0}$ and mean reduced scattering coefficient $\mu'_{s0}$ obtained above is selected out of spread functions preliminarily prepared and stored in the memory unit 70. In this case, because the spread function is selected based on the absorption coefficients and reduced scattering coefficients obtained from the actually measured values, error factors can be eliminated as compared with the case using those values assumed to be suitable.

This "spread function" means a function to indicate the way of spread of light (measurement light) in each voxel, and is a notion involving a so-called weight function as to the effective optical pathlength in each voxel and a so-called contribution function as to a degree of contribution to measurement light in each voxel. The spread function according to the present invention may be either the above weight function or contribution function. Such spread function is described, for example, in "A Perturbation Model for Imaging in Dense Scattering Media: Derivation and Evaluation of Imaging Operation" (H. L. Graber et al., SPIE vol. IS11), "Initial assessment of a simple system for frequency domain diffuse optical tomography" (B. W. Pogue et al., Phys. Med. Biol. 40 (1995) p. 1709-p. 1729), and Japanese Patent Application No. 8-6619 by the present inventors entitled "Optical CT apparatus and image reconstructing method by optical CT." In the present embodiment, the spread functions are preliminarily prepared using the photon diffusion equation without time terms as described below, according to the producing method described in Japanese Patent Application No. 8-6619.

$$\Delta\Phi - \mu_a D^{-1}\Phi = 0$$

Here, $D=1/\{3(1-g)\mu_a\}=1/3\mu'_s$, $\Phi$: density of photons, D: photon diffusion constant, $\mu_a$: absorption coefficient, $\mu'_s$: reduced scattering coefficient, and g: mean cosine of scattering angle of photon due to the scattering medium. Further, the following shows the photon diffusion equation with time terms, which is preferably used in obtaining the refractive index distribution.

$$\frac{1}{C}\frac{\partial \Phi(r, t)}{\partial t} = D(r)\nabla^2 \phi(r, t) - \mu_a \phi(r, t) + S(r, t) \tag{13}$$

Here, $D(r)=1/\{3(1-g)\mu_a(r)\}=1/3\mu'_s(r)$, $\Phi(r, t)$: density of photon at position r and at time t, C: speed of light in the medium, D: photon diffusion constant, $\mu_a$: absorption coefficient, S(r, t): light source, $\mu'_s$: reduced scattering coefficient, t: time, r: position, and g: mean cosine of scattering angle of photon due to scattering medium. Letting C' be the speed of light in a vacuum and n be a refractive index of a measured object, C=C'n.

A spread function fitting the mean absorption coefficient $\mu_{a0}$ and mean reduced scattering coefficient $\mu'_{s0}$ is specifically a function to indicate the way of spread of light that would be obtained if the same relative relation of light incidence-light detection positions as in actual measurement were set for an object having the same mean absorption coefficient and mean reduced scattering coefficient as the mean absorption coefficient and mean reduced scattering coefficient of the measured object and having the same shape as that of the measured object, which is selected based on the mean absorption coefficient $\mu_{a0}$ and mean reduced scattering coefficient $\mu'_{s0}$ and the like.

The memory unit 70 may be arranged to store a correction term for correcting distortion occurring when the object is divided into plural blocks (voxels), and in that case the aforementioned measured values and/or the aforementioned reference values can be corrected in the processing unit 60

(S140). This correction concerning the voxels is such that, for example when total distances are different on the voxels depending upon the cutting way of voxels though the distance is the same between the light incidence position a and the light detection positions b, c, for example, a difference between them is utilized as a correction term for the measured values and/or reference values.

5) Subsequently, the processing unit 60 calculates a change amount $\Delta\mu_a$ in absorption coefficient in each aforementioned region of the plural regions divided into, using the plurality of measured values obtained by the aforementioned plurality of combinations, the aforementioned reference values, and the aforementioned spread function (S150), and outputs it (S160).

Specifically, a change amount in absorption coefficient is obtained using the foregoing reference value of each angle, the foregoing measured values, and the foregoing spread function. The relation holding on that occasion, when considered in correspondence to above Eq. (4), is such that the reference value $I_{d0}$, for example where the positional relation of light incidence-light detection is 180 degrees, is I(ave__180) and the measured values $I_{d1}$ are I(1, 7), I(2, 8), I(3, 9), I(4, 10), I(5, 11), and I(6, 12). At this time, the absorption coefficient of the reference value $I_{d0}$ is the mean absorption coefficient of the inside of the scattering medium SM. Further, letting Wθ be the spread function where the positional relation of light incidence-light detection is 180 degrees, Eq. (4-1) to Eq. (4-6) below hold, and when these simultaneous equations (the simultaneous equations of above Eq. (8)) are obtained every positional relation (i.e., simultaneous equations in the same number as the number of unknowns) and when they are solved, the change amount $\Delta\mu_a$ in absorption coefficient in each region is yielded.

$$\ln(I(ave\_180)) - \ln(I(1, 7)) = \sum_{j=1}^{n} W_{\theta j}\Delta\mu_{a j} \quad (4\text{-}1)$$

$$\ln(I(ave\_180)) - \ln(I(2, 8)) = \sum_{j=1}^{n} W_{\theta j}\Delta\mu_{aj} \quad (4\text{-}2)$$

$$\ln(I(ave\_180)) - \ln(I(3, 9)) = \sum_{j=1}^{n} W_{\theta j}\Delta\mu_{aj} \quad (4\text{-}3)$$

$$\ln(I(ave\_180)) - \ln(I(4, 10)) = \sum_{j=1}^{n} W_{\theta j}\Delta\mu_{aj} \quad (4\text{-}4)$$

$$\ln(I(ave\_180)) - \ln(I(5, 11)) = \sum_{j=1}^{n} W_{\theta j}\Delta\mu_{aj} \quad (4\text{-}5)$$

$$\ln(I(ave\_180)) - \ln(I(6, 12)) = \sum_{j=1}^{n} W_{\theta j}\Delta\mu_{aj} \quad (4\text{-}6)$$

For obtaining a spatial distribution of change amount of absorption coefficient or a spatial distribution of concentration change inside the scattering medium SM, the thus holding relations may be solved with simultaneous equations of the same number as the number of voxels (volume elements) obtained by dividing the inside of scattering medium SM. In the present embodiment the conjugate gradient method was employed. Even if the number of equations is smaller or greater than the number of voxels, a distribution of internal property will be obtained by using the singular value decomposition method or the like, because it changes a singular problem to a non-singular problem.

An absorption distribution concerning absorption coefficient change amounts inside the measured object is obtained based on the change amount $\Delta\mu_a$ in absorption coefficient in each region thus obtained, and an image indicating the distribution is displayed in the display unit 80 (S170).

There are a variety of other methods known as methods for obtaining the absorption distribution from the calculation method of $\Delta\mu_a$ in the processing unit 60 and displaying the image as described above. Such methods are described, for example, in "Optical Back Projection Tomography in Heterogeneous Diffusive Media" (S. B. Cloak et al., in Advances in Optical Imaging and Photon Migration, 1996 Technical Digest; Optical Society of America, Washington D.C., 1996, pp. 147–149), "Back-projection image reconstruction using photon density wave in tissues" (S. A. Walker et al., SPIE vol. 2389, pp. 350, 1995), "Optical tomography by the temporally extrapolated absorbance method" (Ichiro Oda et al., APPLIED OPTICS, vol. 35, No. 01, 1996), and so on. These methods are back projection methods or modifications thereof, which are methods for reconstructing images, in place of the above algorithm.

It is also possible to calculate an absolute value of a concentration difference of an absorptive constituent in each region from the above change amount $\Delta\mu_a$ in absorption coefficient in each region using a known molar absorption coefficient of the absorptive constituent (S180), a distribution concerning concentration differences of the absorptive constituent inside the measured object is obtained based on the absolute value of concentration difference of absorptive constituent in each region thus obtained, and an image indicating the distribution is displayed in the display unit 80 (S190).

Further, it is possible to calculate an absolute value $\mu_a$ of absorption coefficient in above each region using the above change amount $\Delta\mu_a$ in absorption coefficient in each region and the foregoing mean absorption coefficient $\mu_{a0}$ (S200), a distribution concerning absolute values of absorption coefficient inside the measured object is obtained based on the absolute value $\mu_a$ of absorption coefficient in each region thus obtained, and an image indicating the distribution is displayed in the display unit 80 (S210).

Yet further, it is possible to calculate a concentration of an absorptive constituent in each region from the above absolute value $\mu_a$ of absorption coefficient in each region using the known molar absorption coefficient of the absorptive constituent (S220), a distribution concerning concentrations of the absorptive constituent inside the measured object is obtained based on the concentration of the absorptive constituent in each region thus obtained, and an image indicating the distribution is displayed in the display unit 80 (S230).

When the scattering medium SM contains at least two absorptive constituents, for example, when the scattering medium contains oxygenated and deoxygenated hemoglobins, a concentration distribution of each absorptive constituent is obtained by using measurement light having at least two wavelengths different from each other in absorption coefficient to those absorptive constituents, obtaining the foregoing measured values and foregoing reference values for each of the measurement light components having the respective wavelengths, and obtaining the absorption coefficient change amount and the absorption coefficient absolute value for each of the measurement light components having the respective wavelengths, based thereon.

Described below is a measurement of concentration of hemoglobin using the above two-wavelength spectroscopy.

Main absorptive constituents in a mammalian brain are water, cytochrome, and oxygenated and deoxygenated hemoglobins. Absorption of water and cytochrome in the near-infrared region is as little as almost negligible with respect to oxygenated and deoxygenated hemoglobins. Oxygenated and deoxygenated hemoglobins have different absorption spectra, as shown in FIG. 6. Further, the skull may be regarded as a scattering medium with respect to near-infrared rays.

Supposing absorption coefficients $\mu_{a1}$ and $\mu_{a2}$ were obtained for light of two wavelengths, wavelengths $\lambda_1$ and $\lambda_2$, by the method described so far in the above sections, the following equations hold in accordance with the Lambert-Beer law.

$$\mu_{a1} = \epsilon_{Hb,1}[Hb] + \epsilon_{HbO,1}[HbO]$$

$$\mu_{a2} = \epsilon_{Hb,2}[Hb] + \epsilon_{HbO,2}[HbO]$$

where $\epsilon_{Hb,1}$: molar absorption coefficient [mm$^{-1}\cdot$M$^{-1}$] of deoxygenated hemoglobin at wavelength $\lambda_1$;

$\epsilon_{HbO,1}$: molar absorption coefficient [mm$^{-1}\cdot$M$^{-1}$] of oxygenated hemoglobin at wavelength $\lambda_1$;

$\epsilon_{Hb,2}$: molar absorption coefficient [mm$^{-1}\cdot$M$^{-1}$] of deoxygenated hemoglobin at wavelength $\lambda_2$;

$\epsilon_{HbO,2}$: molar absorption coefficient [mm$^{-1}\cdot$M$^{-1}$] of oxygenated hemoglobin at wavelength $\lambda_2$;

[Hb]: molar concentration [M] of deoxygenated hemoglobin;

[HbO]: molar concentration [M] of oxygenated hemoglobin.

Therefore, the molar concentration [Hb] of deoxygenated hemoglobin and the molar concentration [HbO] of oxygenated hemoglobin can be obtained from the known parameters $\epsilon_{Hb,1}$, $\epsilon_{HbO,1}$, $\epsilon_{Hb,2}$, $\epsilon_{HbO,2}$, and $\mu_{a1}$ and $\mu_{a2}$ calculated from the measured values.

Quantification of respective concentrations of three components absorption spectra of which are known, as in the case of cytochrome being taken into consideration in addition to the above case, can be carried out using light of three or more wavelengths. In general, concentrations of n constituents absorption spectra of which are known can be quantitatively measured in the same manner as above from measured values of absorption coefficient at n or (n+1) wavelengths.

Further, since the degree of saturation Y is $$Y = [HbO]/([Hb] + [HbO]),$$

using $$\mu_{a1}/\mu_{a2} = [\epsilon_{Hb,1} + Y(\epsilon_{HbO,1} - \epsilon_{Hb,1})]/[\epsilon_{Hb,2} + Y(\epsilon_{HbO,2} - \epsilon_{Hb,2})],$$

the degree of saturation Y can be calculated readily from the known parameters $\epsilon_{Hb,1}$, $\epsilon_{HbO,1}$, $\epsilon_{Hb,2}$, $\epsilon_{HbO,2}$, and $\mu_{a1}$ and $\mu_{a2}$ calculated from the measured values.

In the above method, the present invention permits the absorption coefficients $\mu_{a1}$ and $\mu_{a2}$ for the light of each wavelength to be obtained with accuracy, so that each concentration can also be attained with accuracy. The above equations can be further simplified with use of the wavelength (800 nm, isosbestic wavelength) showing the same value of absorption for oxygenated and deoxygenated hemoglobins.

The foregoing described the preferred embodiment of the present invention, but it is noted that the present invention is by no means limited to the above embodiment, of course.

Figure 9:
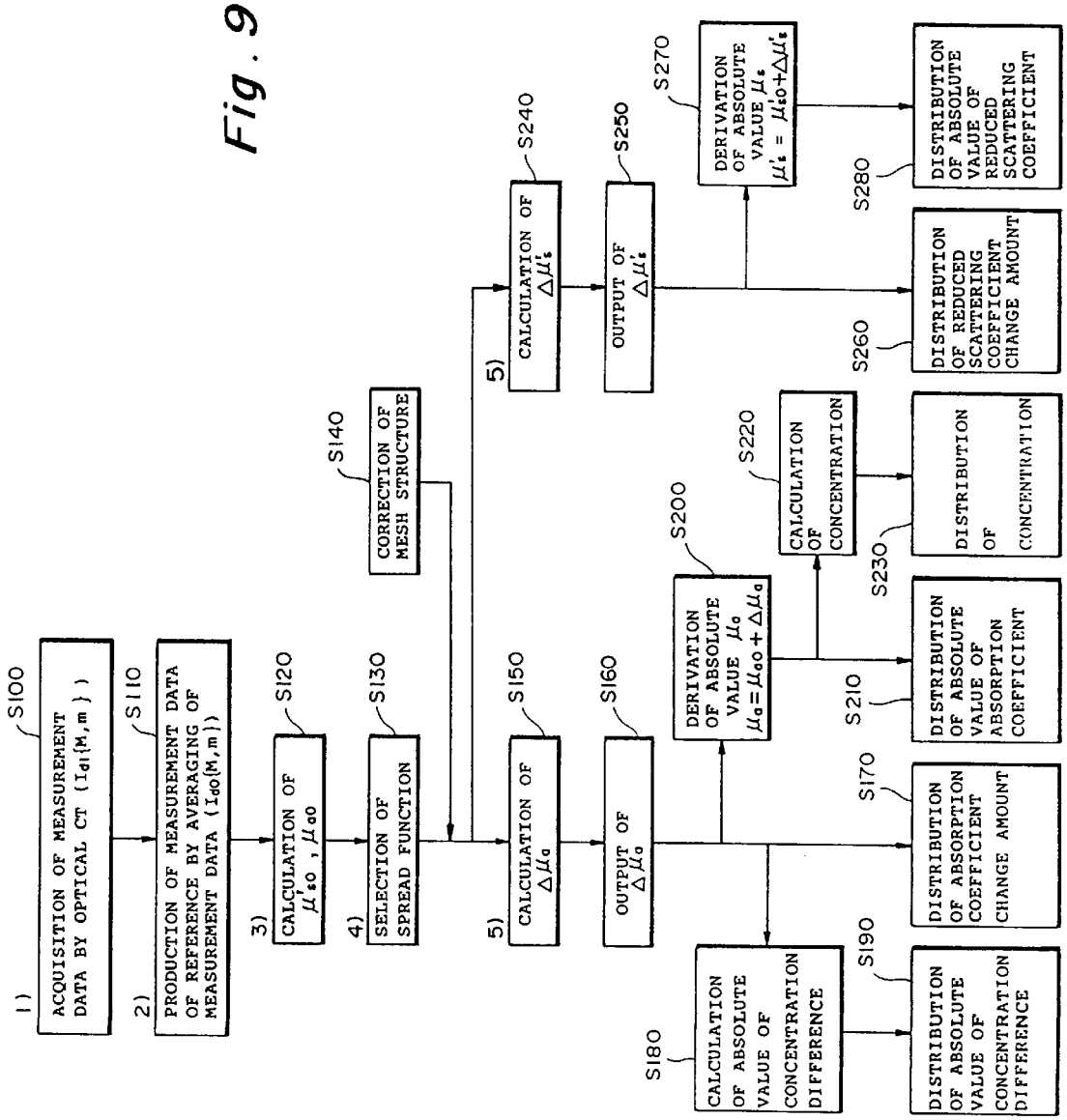
FIG. 9 is a flowchart to show another example of the internal property distribution measuring method of the present invention.

Specifically, the above embodiment was arranged to obtain the absorption coefficient as an internal property, but the present invention can also be applied to measurement of reduced scattering coefficient as described previously. FIG. 9 shows a flowchart of an embodiment to obtain the absorption coefficient and reduced scattering coefficient.

Figure 8:
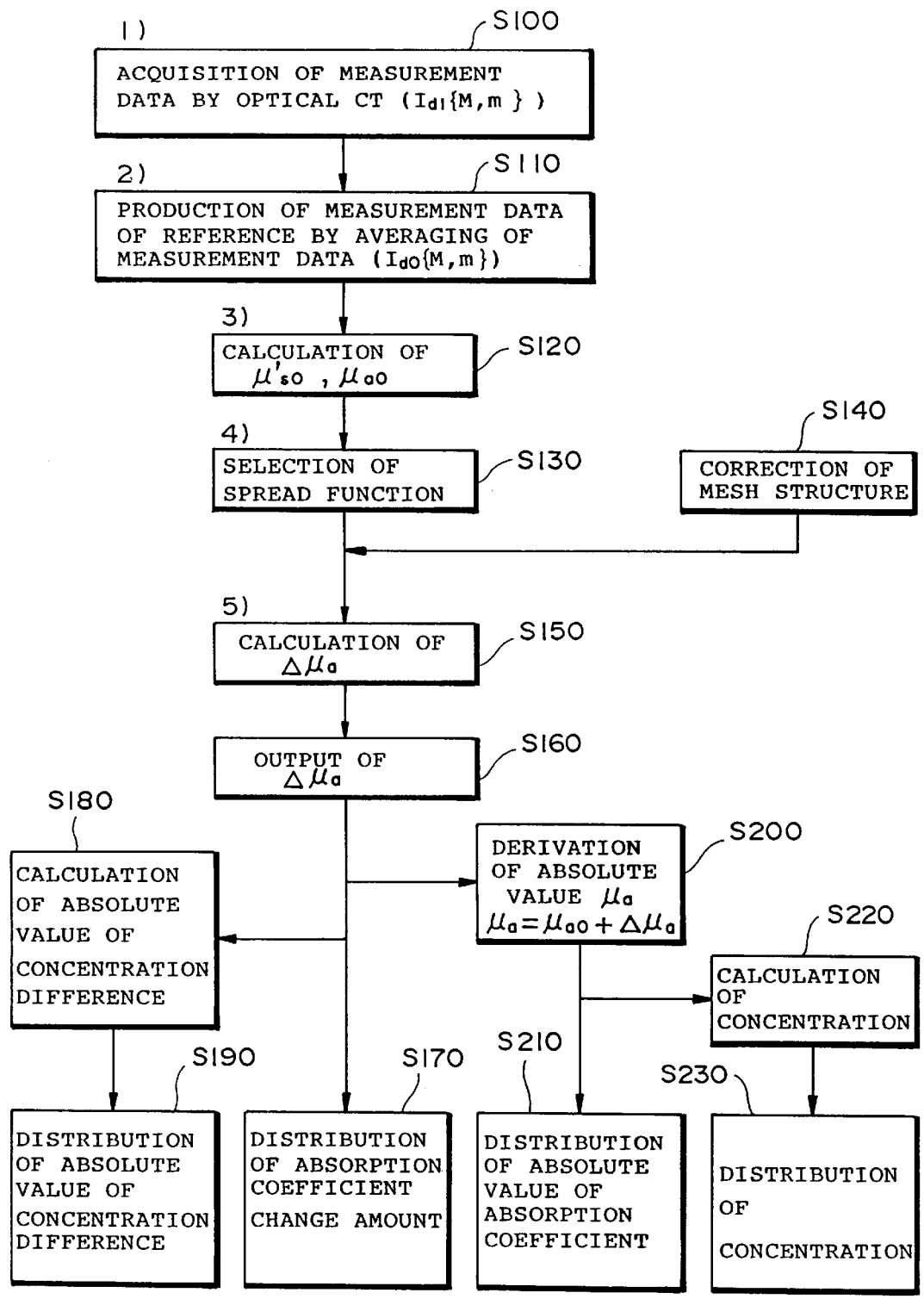
FIG. 8 is a flowchart to show an example of the internal property distribution measuring method of the present invention.

In the method shown in FIG. 9, the measurement of absorption coefficient is carried out in the same manner as in the method shown in FIG. 8, but, in selecting the spread function (W$\theta$) associated with the mean absorption coefficient $\mu_{a0}$ and mean reduced scattering coefficient $\mu'_{s0}$, it is preferable to select the spread function (W$\mu_{a,j}$) for absorption coefficient and the spread function (W$\mu'_{s,j}$) for reduced scattering coefficient (S130).

Then the processing unit 60 calculates the change amount $\Delta\mu'_s$ of reduced scattering coefficient in each region of the plural regions divided into, using the plural measured values obtained by the plurality of combinations, the reference values, and the spread function (S240), and outputs it (S250). Specifically, based on Eq. (4') described previously, the change amount of reduced scattering coefficient is obtained using the reference value of each angle, the measured values, the spread functions, and the change amount of absorption coefficient. More specifically, simultaneous equations hold based on Eq. (4'), similarly as Eq. (4-1) to Eq. (4-6) described previously, and these simultaneous equations are established every positional relation and solved, thereby calculating the change amount $\Delta\mu'_s$ of reduced scattering coefficient in each region.

A reduced scattering coefficient change amount distribution inside the measured object is obtained based on the change amount $\Delta\mu'_s$ of reduced scattering coefficient in each region thus obtained, and an image indicating the distribution is displayed in the display unit 80 (S260).

Further, it is possible to calculate the absolute value $\mu'_s$ of reduced scattering coefficient in each region, using the above change amount $\Delta\mu'_s$ of reduced scattering coefficient in each region and the mean reduced scattering coefficient $\mu'_{s0}$ (S270), a distribution concerning absolute values of reduced scattering coefficient inside the measured object is obtained based on the absolute value $\mu'_s$ of reduced scattering coefficient in each region thus obtained, and an image indicating the distribution is displayed in the display unit 80 (S280).

Figure 10:
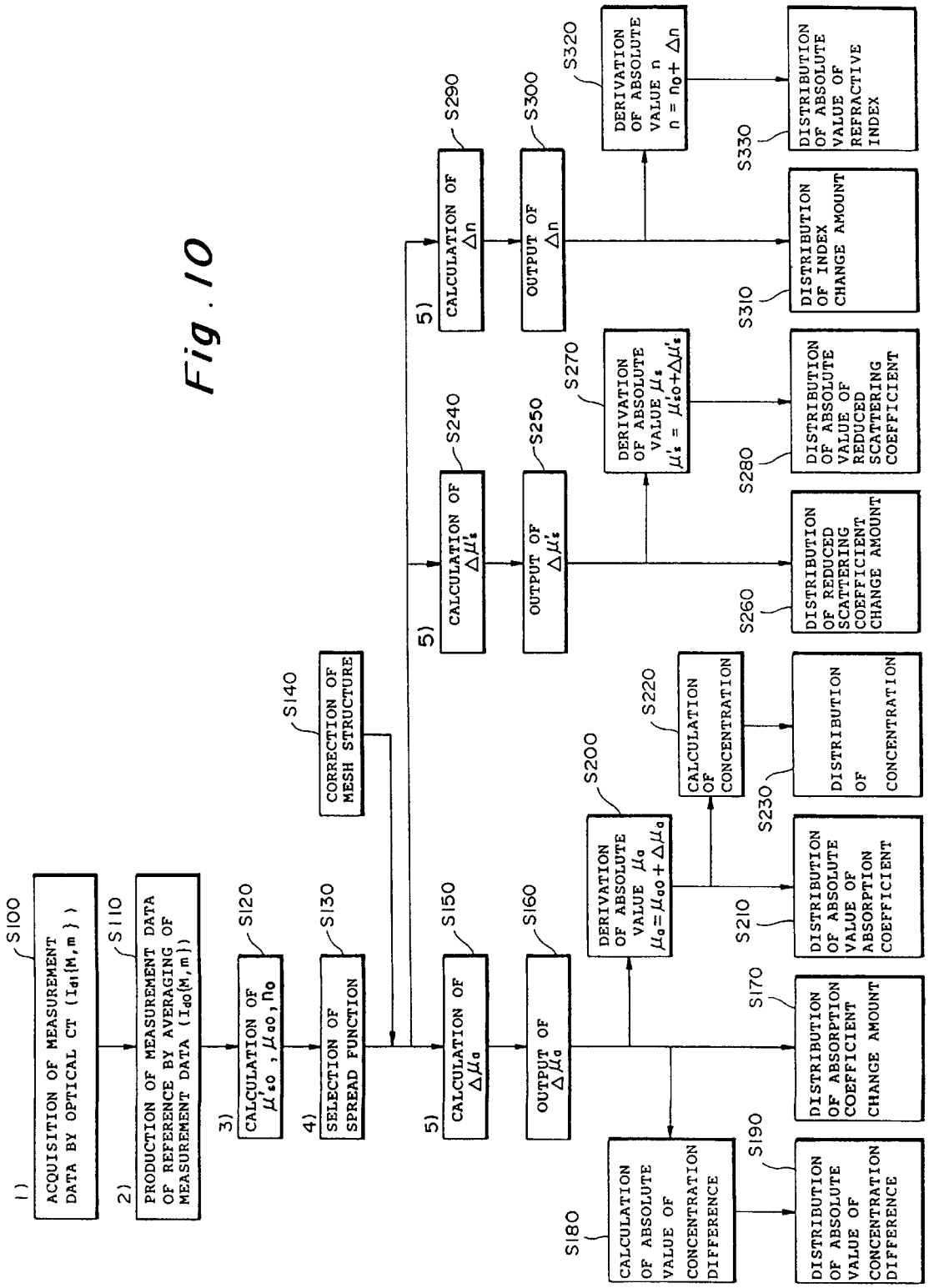
FIG. 10 is a flowchart to show still another example of the internal property distribution measuring method of the present invention.

Additionally, the present invention can also be applied to measurement of refractive index, and FIG. 10 shows a flowchart of an embodiment for obtaining the absorption coefficient, reduced scattering coefficient, and refractive index.

In the method shown in FIG. 10, the measurement of absorption coefficient and reduced scattering coefficient is carried out in the same manner as in the methods shown in FIG. 8 and FIG. 9, but, in obtaining the mean absorption coefficient $\mu_{a0}$ and mean reduced scattering coefficient $\mu'_{s0}$, based on the reference value or the like in each positional relation, a mean refractive index $n_0$ is also obtained (S120). However, the refractive index of water (1.33) may be used as the mean refractive index $n_0$. In selecting the spread function (W$\theta$), it is preferable to select the spread function (W$\mu_{a,j}$) for absorption coefficient, the spread function (W$\mu'_{s,j}$) for reduced scattering coefficient, and the spread function (W$_{n,j}$) for refractive index (S130).

Then the processing unit 60 calculates a change amount $\Delta n$ of refractive index in each region of the plural regions divided into as described above, using the plural measured values obtained by the plurality of combinations, the reference values, and the spread function (S290), and outputs it (S300). Specifically, based on Eq. (4'') described previously, the change amount of refractive index is obtained using the reference value of each angle, the measured values, the spread functions, the change amount of absorption coefficient, and the change amount of reduced scattering coefficient. More specifically, simultaneous equations hold based on Eq. (4"), similarly as Eq. (4-1) to Eq. (4-6) described previously, and these simultaneous equations are established every positional relation and solved, thus calculating the change amount Δn of refractive index in each region.

A refractive index change amount distribution inside the measured object is obtained based on the change amount Δn of refractive index in each region thus obtained and an image indicating the distribution is displayed in the display unit 80 (S310).

Further, it is possible to calculate the absolute value n of refractive index in above each region, using the above change amount Δn of refractive index in each region and the mean refractive index $n_0$ (S320), a distribution concerning absolute values of refractive index inside the measured object is obtained based on the absolute value n of refractive index in each region thus obtained, and an image indicating the distribution is displayed in the display unit 80 (S330).

Once the distribution concerning the refractive indices is attained in this way, it becomes possible to obtain a distribution of blood glucose concentration. A method for detecting the blood glucose concentration by a change of refractive index is, for example, the method described in "Possible correlation between blood glucose concentration and the reduced scattering coefficient of tissues in the near infrared" (John S. Maier et al., OPTICS LETTERS vol. 19, No. 24, Dec. 15, 1994). The glucose concentration of organism tissue greatly affects the refractive index of extracellular fluid and the reduced scattering coefficient in tissue is greatly dependent upon an index difference between extracellular fluid and cell. Thus, a change in the refractive index of extracellular fluid will result in affecting detected light. It becomes thus possible to obtain a distribution of blood cell concentration inside tissue by obtaining a refractive index distribution based on the detected light.

Figure 11:
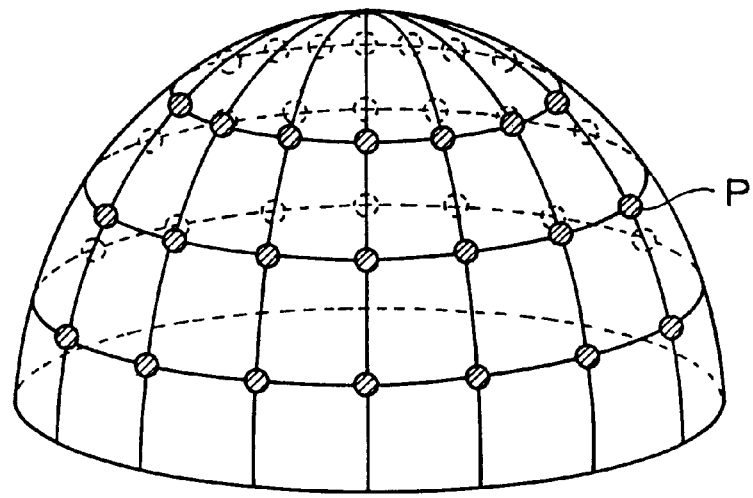
FIG. 11 is a schematic drawing to show an example of arrangement of light incidence and/or light detection positions according to the present invention.
Figure 12:
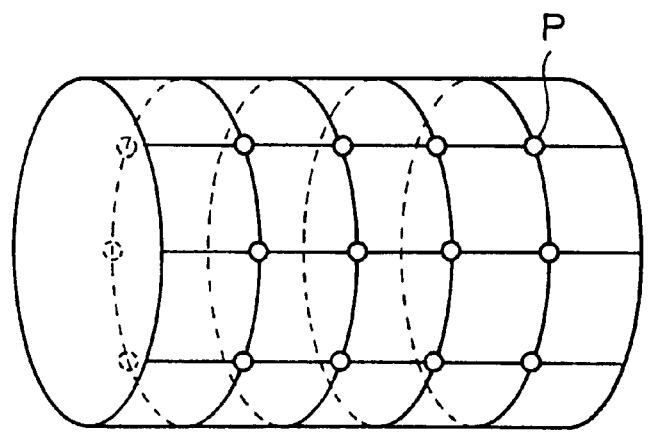
FIG. 12 is a schematic drawing to show another example of arrangement of light incidence and/or light detection positions according to the present invention.

In the above embodiment the plural light incidence and light detection positions were positioned around one cross section of the scattering medium, but the light incidence and/or light detection positions (which will be denoted by P) may be arranged stereoscopically as shown in FIG. 11 or FIG. 12. Namely, when the measured object is assumed to be a head or a mamma, the light incidence and/or light detection positions (P) may be placed as shown in FIG. 11; when the measured object is assumed to be an arm, a leg, a breast, or a mamma (under pressure), the light incidence and/or light detection positions (P) may be placed as shown in FIG. 12.

The above embodiment employed the measured values of light quantity by the time integration method, as measured values, but the measured values applicable to the present invention are not limited to these. For example, they may be those of phase difference (or phase delay) or amplitude of measurement light. In addition, a specific technique for acquiring the measured values in the processing unit 60 may be properly selected depending upon desired measured values, and, for example, such means may be employed as phase difference and/or amplitude measurement by the phase modulation method or as time-resolved waveform measurement by the time-resolved spectroscopy.

Figure 13:
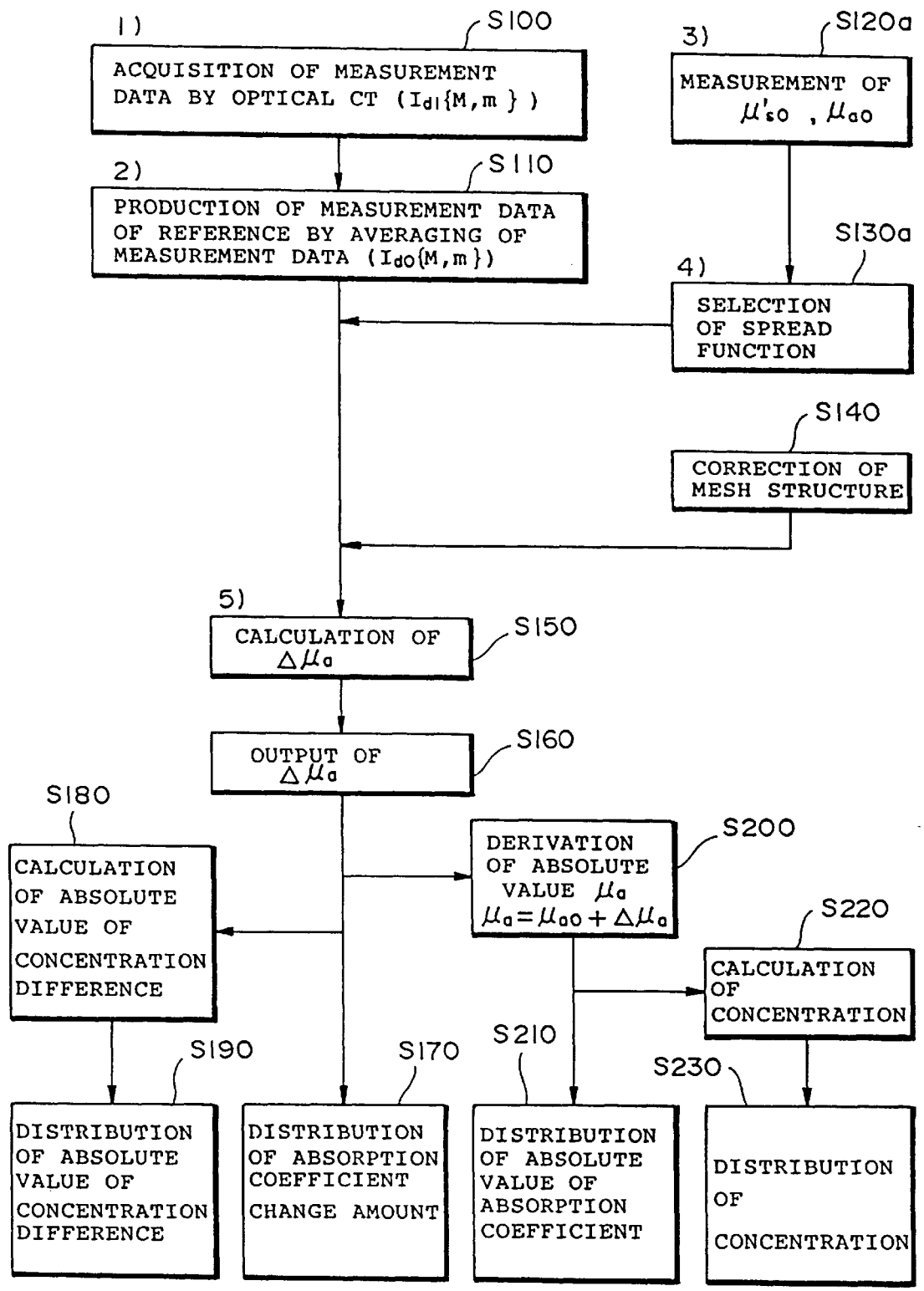
FIG. 13 is a flowchart to show still another example of the internal property distribution measuring method according to the present invention.
Figure 14:
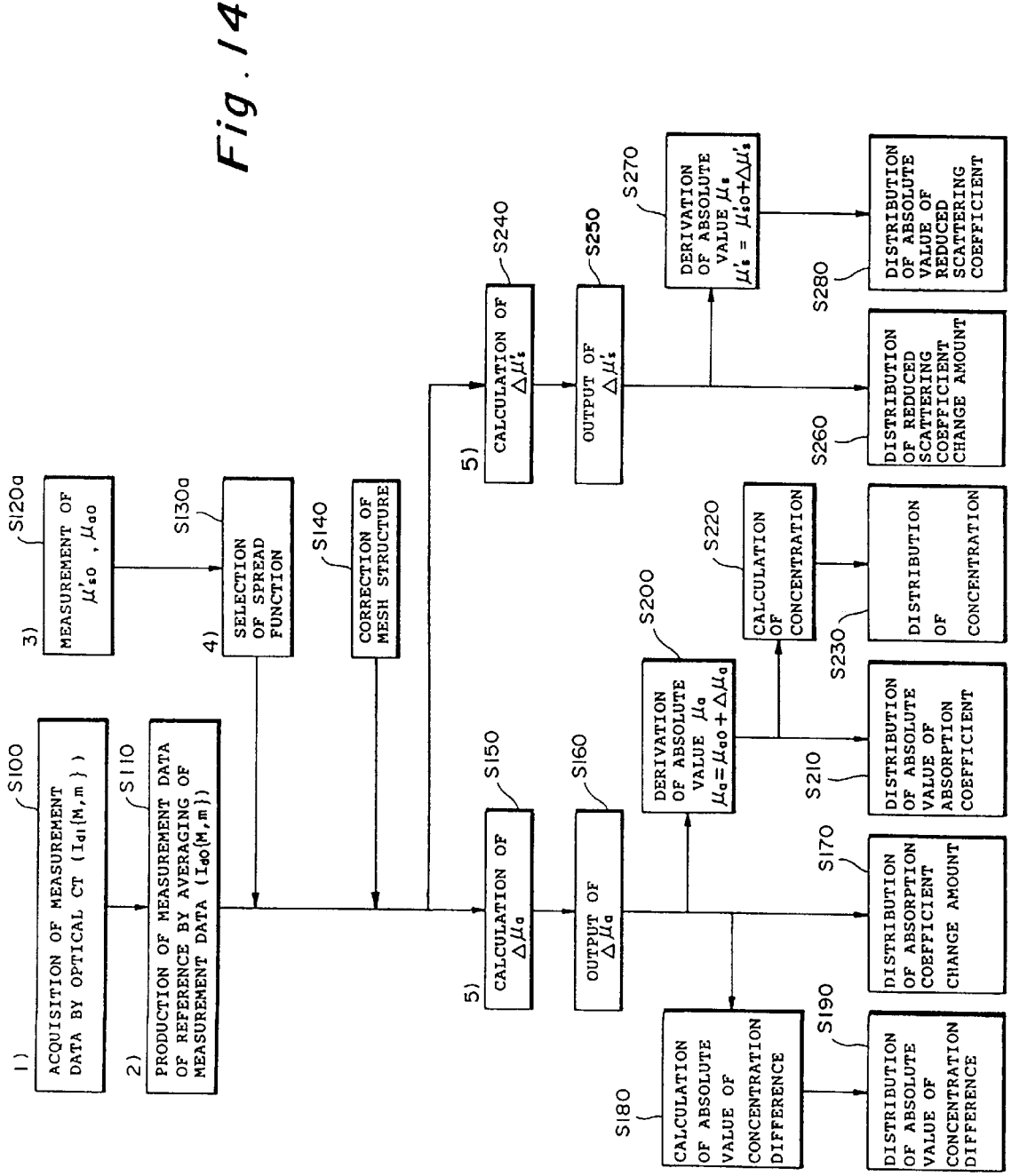
FIG. 14 is a flowchart to show still another example of the internal property distribution measuring method according to the present invention.
Figure 15:
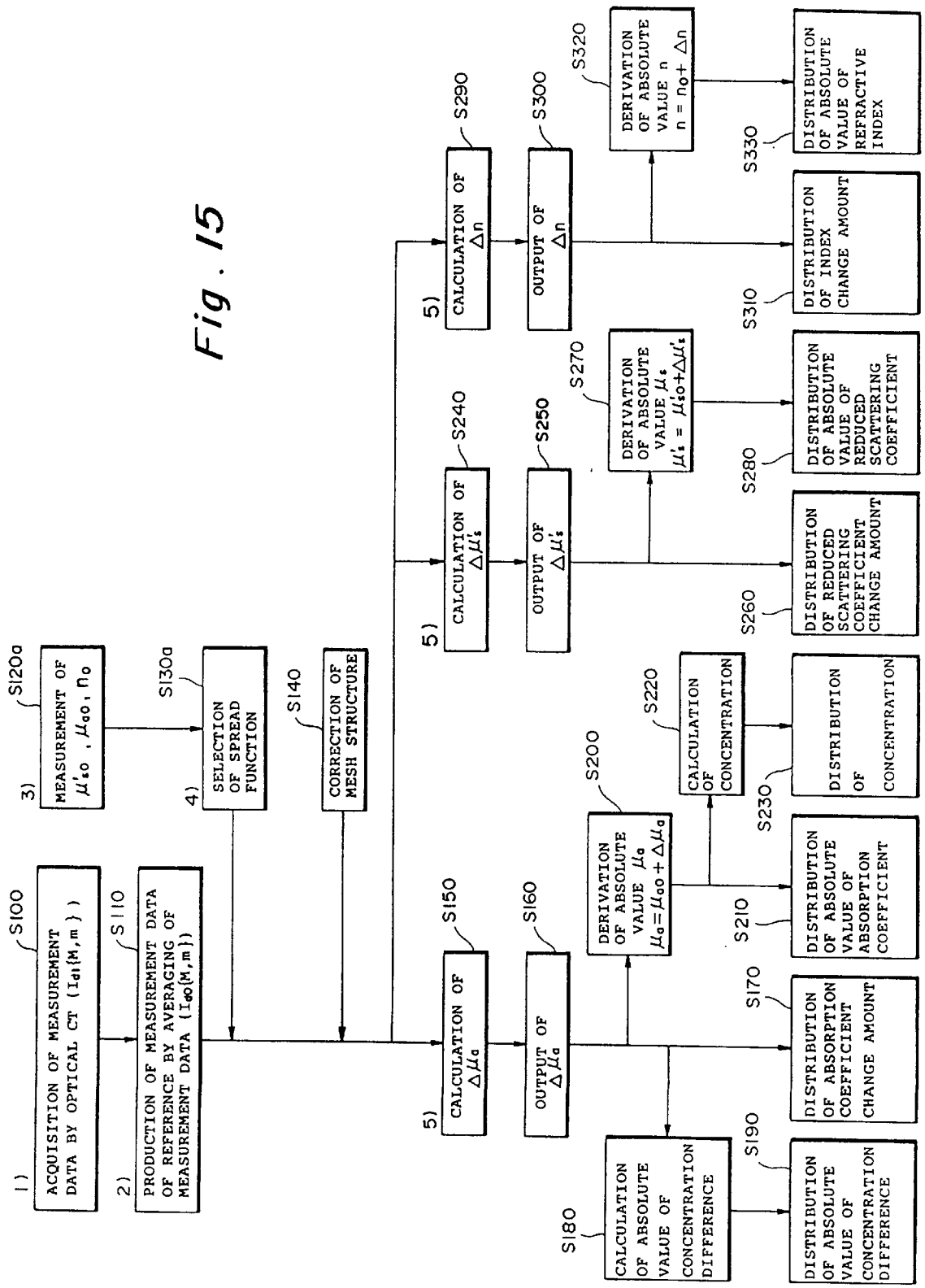
FIG. 15 is a flowchart to show still another example of the internal property distribution measuring method according to the present invention.

In the above embodiment the mean absorption coefficient and mean reduced scattering coefficient inside the scattering medium SM were obtained from the data obtained by the optical CT apparatus itself according to the present invention, but it is also possible to obtain the mean absorption coefficient and mean reduced scattering coefficient inside the scattering medium SM by another apparatus (S120a) and select the spread function based thereon (S130a) as shown in FIG. 13 to FIG. 15. The steps other than the above in FIG. 13 to FIG. 15 each correspond to the steps in FIG. 8 to FIG. 10. An advantage in this case is the simple configuration of the system of optical CT apparatus, because, for example, data obtained by the optical CT apparatus can be measured by CW (continuous-wave light) and the pulsed light or modulated light is used only in the apparatus for obtaining the mean absorption coefficient and mean reduced scattering coefficient. A technique for obtaining the mean absorption coefficient and mean reduced scattering coefficient by another apparatus may be the phase modulation method or the time-resolved spectroscopy.

Methods for measuring the mean reduced scattering coefficient $\mu'_{s0}$ and mean absorption coefficient $\mu_{a0}$ as regarding the distribution of optical parameter as uniform inside the measured object in this way are described, for example, in "Development of Time Resolved Spectroscopy System for Quantitative Non-invasive Tissue Measurement" M. Miwa et al., SPIE vol. 2389 as to the time-resolved spectroscopy and, for example, in the bulletin of Japanese Laid-open Patent Application No. 6-221913 as to the phase modulation method. If the optical CT apparatus incorporates the above technique, it will be able to perform the calculation at the same time as acquisition of the measured values.

Figure 16A:
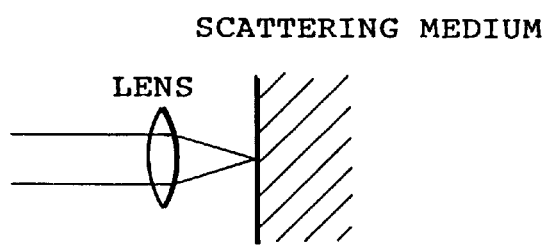
FIGS. 16A, 16B, 16C and 16D are schematic drawings each to show an example of the light incidence method into the scattering medium.
Figure 16B:
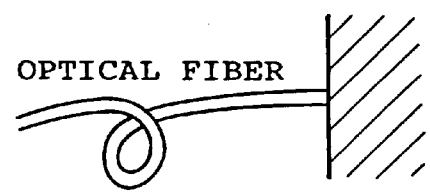
Figure 16C:
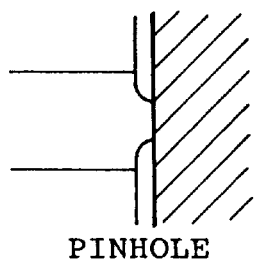
Figure 16D:
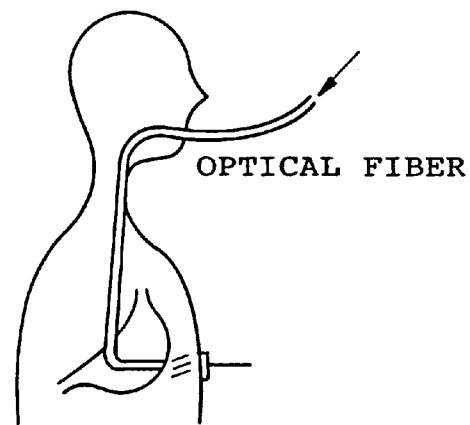

Means for launching light into the scattering medium such as a living body, other than the method using the optical fibers shown in FIG. 4 and FIG. 16B, may be any method utilizing a condenser lens (FIG. 16A) or a pinhole (FIG. 16C), any method for launching light from the inside of body as in a gastrocamera (FIG. 16D), and so on.

Since the mean diffusion length is approximately 2 mm in the scattering medium such as a living sample, incident light is scattered before it propagates about 2 mm straight, thus losing directionality of light. Therefore, influence of mean diffusion length is negligible in the case of scattering media with thickness of several cm or more, and thus the light may be made incident in a spot shape. Also, a thick beam of light may be made incident into the scattering medium. In this case, the beam may be regarded as a plurality of spot light sources arranged.

In the embodiment shown in FIG. 4 the space is fine between the light incidence fiber and light detection fiber and the surface of scattering medium SM. In practical applications, this may be increased and this space may be filled with a liquid or a jelly substance (hereinafter referred to as an interface material) having the refractive index and reduced scattering coefficient nearly equal to those of the scattering medium SM being a measured object. Namely, no problem will arise, because the light is incident into the measured object as diffusely propagating in the interface material. When reflection on the surface of scattering medium SM is not negligible, proper selection of the interface material can decrease influence of surface reflection or the like. Further, in a case where a space between the light incidence fiber and/or light detection fiber and the surface of scattering medium SM such as a living sample is filled with such an interface material, a plurality of combinations of the light incidence position and the light detection position the positional relation of which is relatively identical can be easily and surely attained.

Figure 7B:
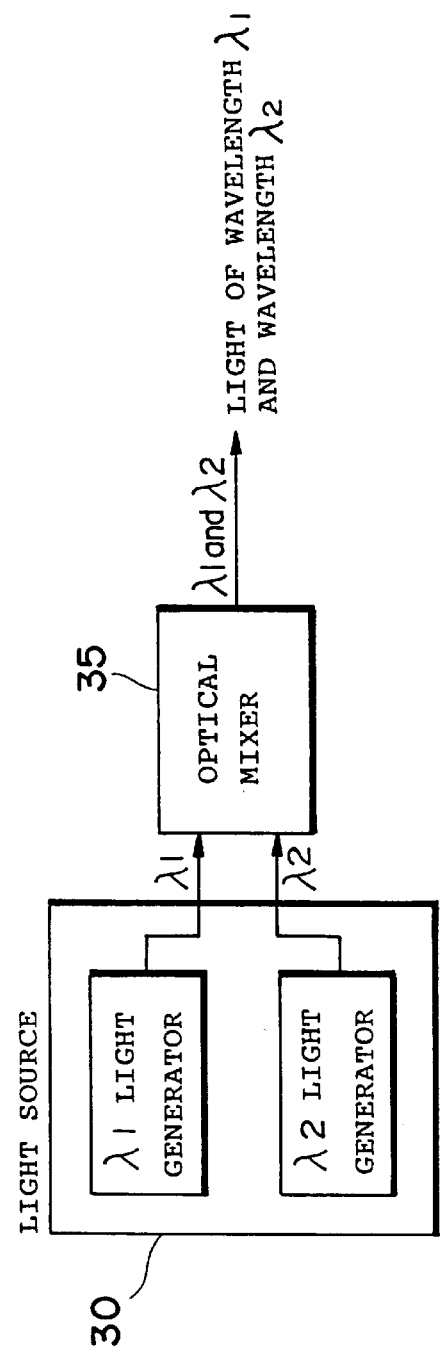
Figure 17:
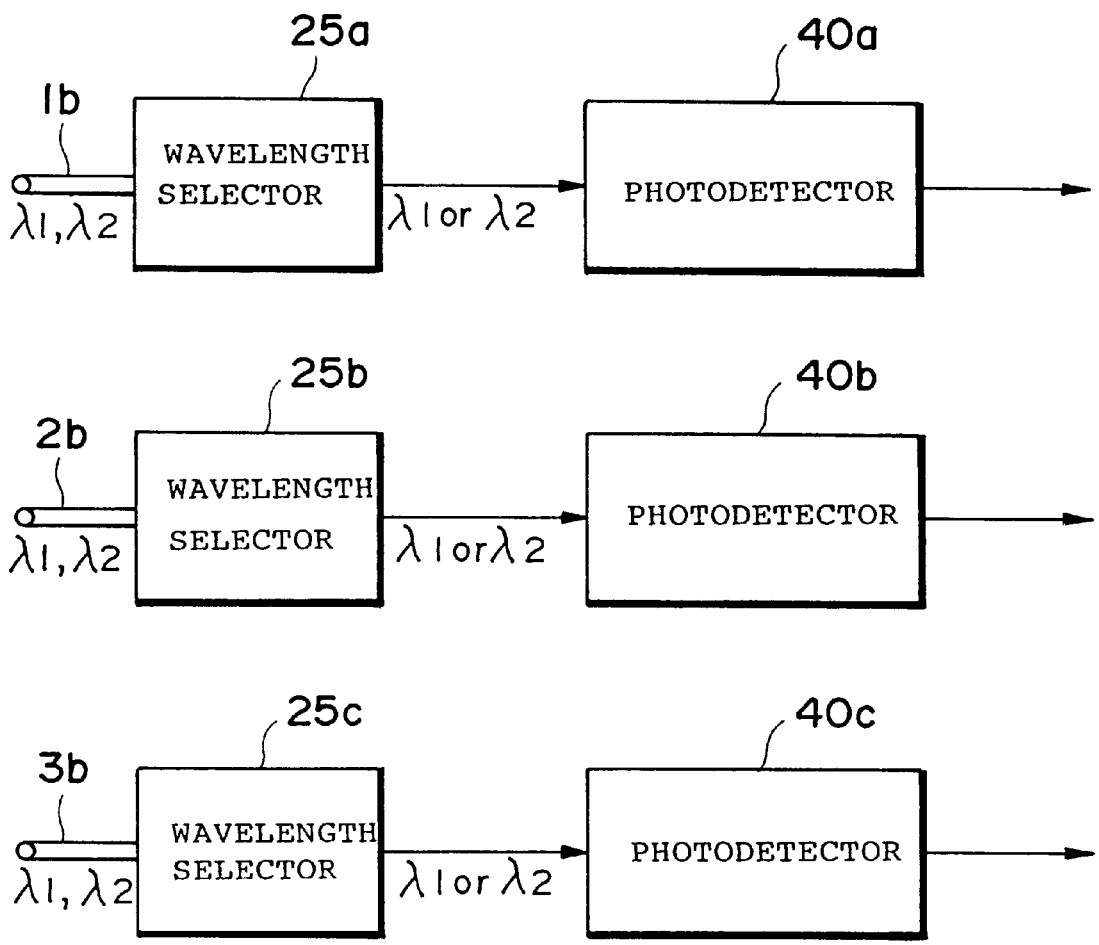
FIG. 17 is a schematic drawing to show an example of the light detecting means.

Further, the above embodiment was described in an aspect using the light of different wavelengths as being launched in time division, but it is also permissible to employ a method for coupling light components of different wavelengths into coaxial beams by an optical coupler 35, selecting a wavelength by a wavelength selecting filter 20 provided immediately before an incident point of light, and letting light of each wavelength enter the scattering medium, or a method for letting the beams in parallel into the scattering medium as they are (FIG. 7B). In the case of the latter, it is, however, necessary to subject the detected light to wavelength selection by wavelength selecting filters 25a to 25c disposed immediately before the photodetectors 40a to 40c, as shown in FIG. 17.

Figure 18A:
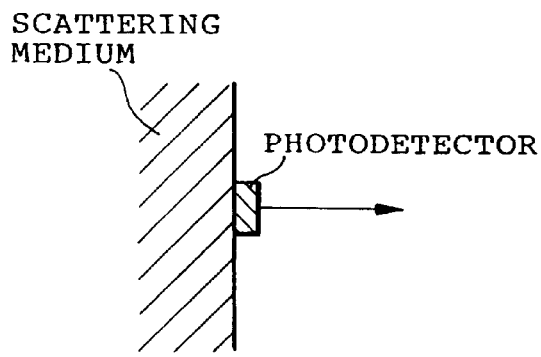
FIGS. 18A, 18B and 18C are schematic drawings each to show an example of the light detecting method.
Figure 18B:
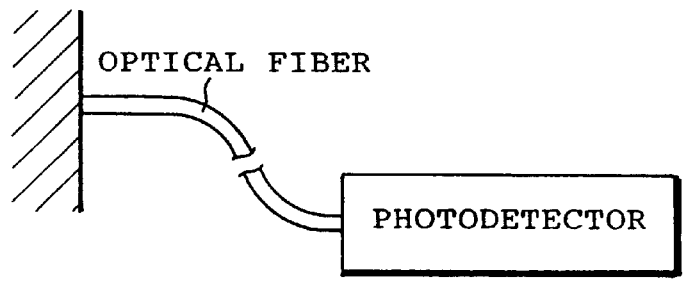
Figure 18C:
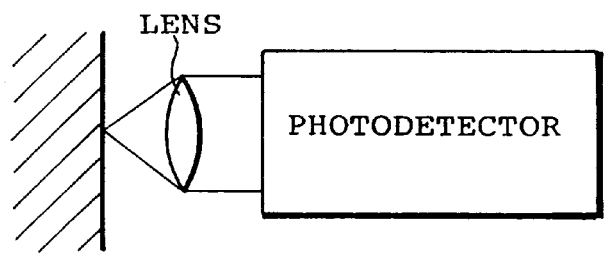

Means for receiving and detecting the light having propagated diffusely inside the scattering medium, other than the method using the optical fibers as shown in FIG. 4 and FIG. 18B, may be a direct detecting method (FIG. 18A), a method using a lens (FIG. 18C), and so on.

When signals obtained by the photodetector 40 need to be amplified with low noise, a narrow-band amplifier (FIG. 19A), a lock-in amplifier (FIG. 19B), or the like may be utilized. In the case of the lock-in amplifier being used, the aforementioned synchronous signal is used as a reference signal. This method is effective in performing measurement in a high dynamic range, using the rectangular-wave light or pulsed light.

Further, in the above embodiment a plurality of light incidence fibers and light detection fibers were positioned around the scattering medium and the light incidence position and light detection position were moved by successively changing the fibers respectively used for light incidence and for light detection, but the light incidence position and light detection position to the scattering medium may be scanned in synchronism. This arrangement permits an image indicating a distribution of internal information to be obtained by obtaining the internal information of each part of the scattering medium, storing it in a frame memory, and reading it by a television system. Further, measurements at different times allow a temporal change of internal information to be measured. The aforementioned memory unit 70 has a function to store the internal information thus obtained and the display unit 80 displays an intermediate status or a result thereof. In this case, these arithmetic processes can be executed at high speed by the computer device 60 provided with the memory 70, the display 80, and so on.

With using still another method, as described in the bulletin of Japanese Laid-open Patent Application No. 6-221913 or in the bulletin of Japanese Laid-open Patent Application No. 6-129984, wherein a regularly circular holder is set around the measured object and measurement is carried out therein, differences among individuals are absorbed therein even in measuring the human head, and the measurement can be conducted in the state of the actual measurement system being close to the model system, thus tending to improve the accuracy.

At least two light incidence positions and at least two light detection positions may be previously settled so that the positional relations of the combinations of the light incidence positions and the light detection positions become relatively identical. In this case, it becomes easy to obtain measured values at the combinations the positional relation of which is relatively identical and to calculate a mean value of the measured values.

The above embodiment was arranged to calculate the spatial distribution of absorption coefficient from the known reduced scattering coefficient, but the spatial distribution of reduced scattering coefficient can also be obtained from the known absorption coefficient by the same technique. It is thus possible to obtain the spatial distributions of the both absorption coefficient and reduced scattering coefficient by the technique proposed this time.

The above embodiment used the photon diffusion equation as an equation for obtaining the internal property, but the equation does not always have to be limited to it. For example, it is also permissible to use an equation derived from the fact that absorption of light inside the scattering medium can be expressed as a function of propagation distance, to use a relational equation between detected light and internal property obtained empirically, or the like.

If correlation is attained between a disease or a body condition and the detected light, the present invention will enable to acquire useful information directly from the detected light. For example, when there is the correlation between a change of detected light and a structural change of tissue, the structural change can be obtained from the detected light utilizing the correlation.

EXAMPLE

The following example shows an example of imaging of absorption coefficient when only the absorption coefficient is changed among the all internal properties (absorption coefficient, reduced scattering coefficient, refractive index, etc.) which the object has.

In order to prove effectiveness of the present invention, experiments were conducted in the following procedures using the same apparatus as the one shown in FIG. 4 except that the intervals of locations of the light incident fibers were 20 degrees and the intervals of locations of the light detection fibers were 10 degrees. Since the phantom used in this example has the same shape in the direction along the height (or since it has symmetry in the z-axis direction), the 3-D (stereoscopic) problem can be dimensionally decreased to a 2-D (cross-sectional) problem.

Figure 20A:
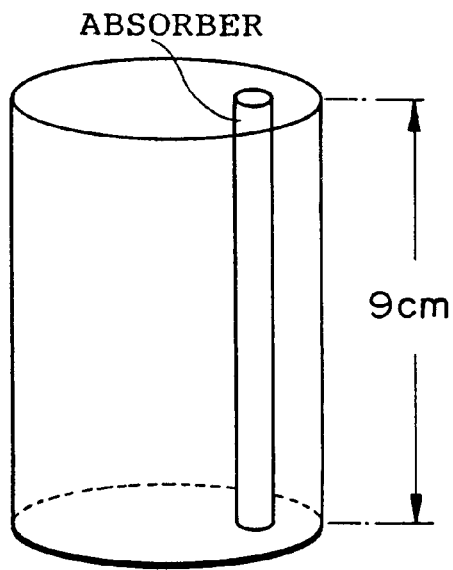
FIGS. 20A and 20B are a perspective view and a top plan view, respectively, of the phantom used in the example.
Figure 20B:
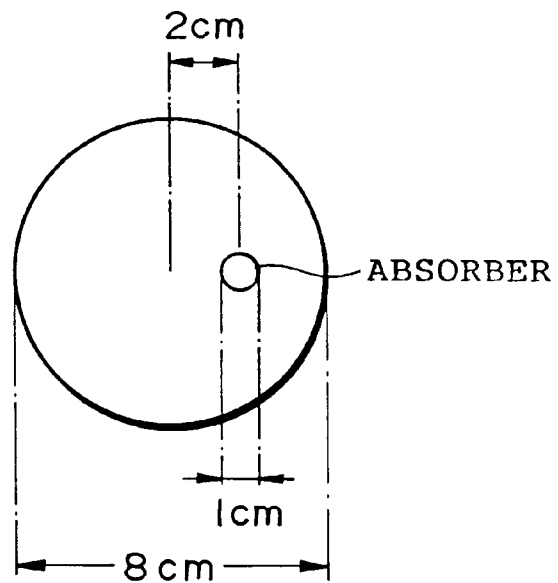

Specifically, the laser of CW light having the wavelength 800 nm and the power 50 mw was made incident through the light incidence fibers into the phantom shown in FIGS. 20A and 20B, and the light transmitted or scatteredly reflected by the phantom was detected by the light detection fibers to be guided to the detector. Specifications of the phantom used were as follows.

(Material) Matrix=epoxy resin
  Scattering substance=silica particles
  Absorptive substance=dyes
(Shape) Cylindrical solid phantom
  Diameter=8 cm
  Height=9 cm
(Matrix) Absorption coefficient=0.01/mm
  Reduced scattering coefficient=1.00/mm
(Absorptive substance) Diameter=1 cm
  Absorption coefficient=0.02/mm
  Reduced scattering coefficient=1.00/mm Light signals detected were converted to detection signals by a photomultiplier tube and the detection signals were added for ten seconds as being read by a counter. The sum was sent through GPIB (measurement interface bus to the computer.

Figure 21:
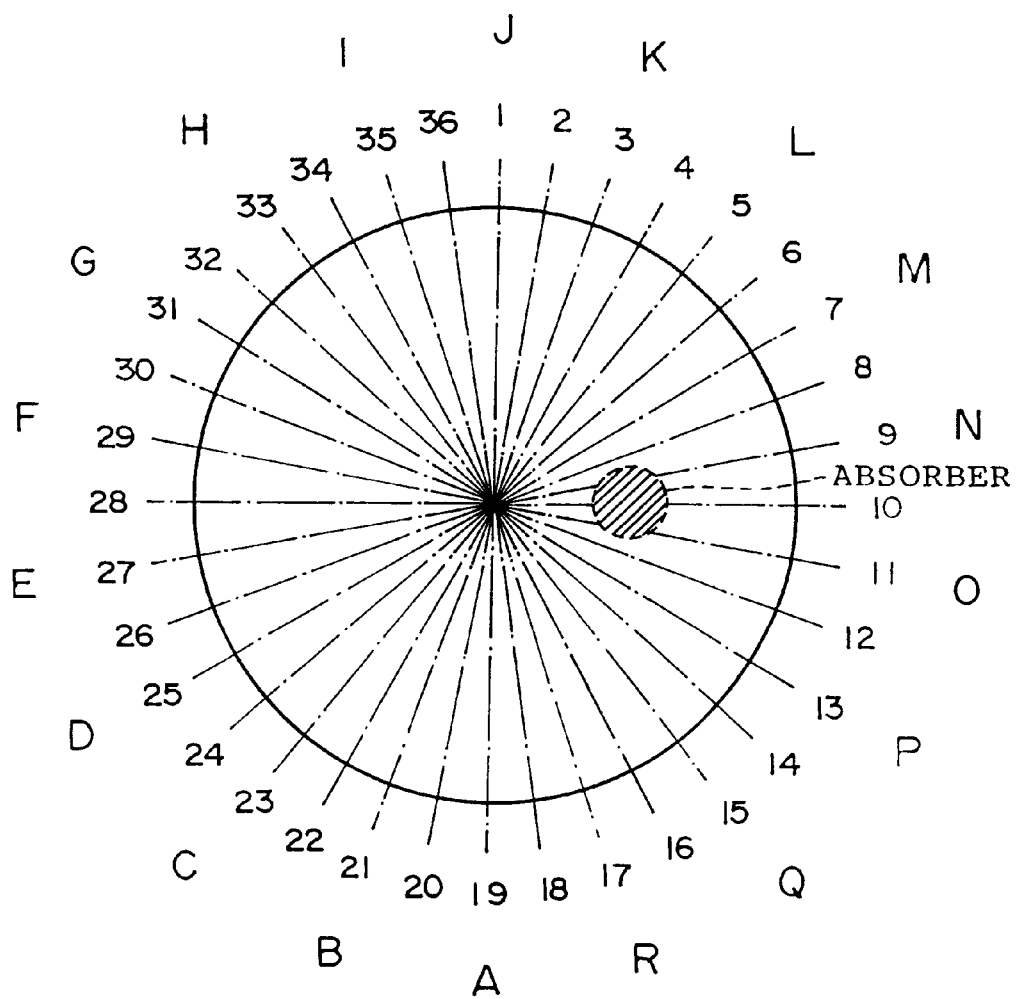
FIG. 21 is an auxiliary drawing for explaining the relation between the light incidence positions and light detection positions in the example.

Defining the measurement up to this point as one measurement, data was acquired with clockwise movement of light incidence fiber every 20 degrees from A to R shown in FIG. 21 and with clockwise movement of light detection fiber every 10 degrees. Light detection positions per light incidence position were ten locations from 0 degree to 90 degrees with respect to the reference of each light incidence position.

Experiment results are as follows.

1) The reference value $I_{d0}$ was acquired with a phantom without absorptive substance prepared separately, and an image was reconstructed. The result is shown in FIG. 22A (in which the background is black and the index of absorption coefficient is shown in FIG. 22B). In the image shown in FIG. 22A a plurality of images appear and positional deviation occurs. The circle illustrated in FIG. 22A indicates the position of image expected.

Figures 23A, 23B:
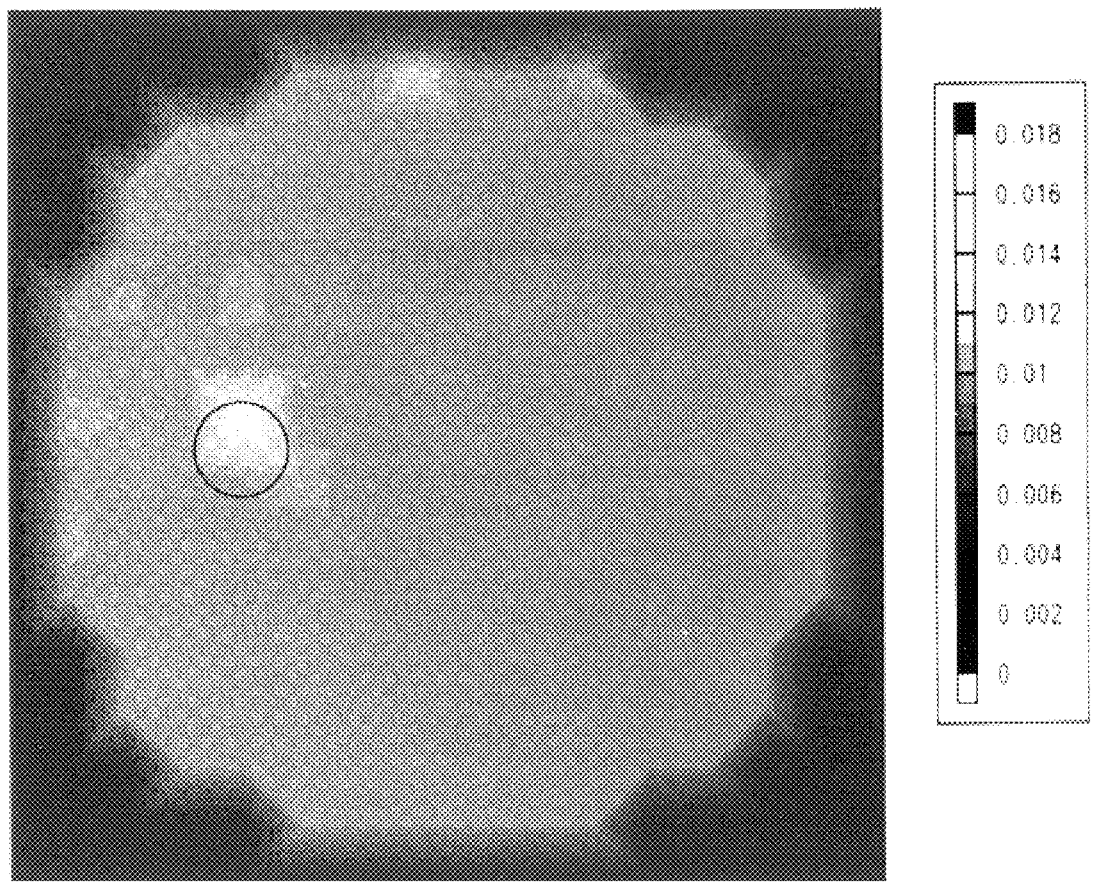
FIGS. 23A and 23B are photographs to show a half-tone image displayed on the display as a result of reconstruction of image by the method of the present invention.

2) According to the present invention, the mean value of measured values was obtained every combination of light incidence-light detection positions the positional relation of light incidence-light detection of which was relatively identical and an image was reconstructed using the mean value as the reference value $I_{d0}$. The result is shown in FIG. 23A (in which the background is black and the index of absorption coefficient is shown in FIG. 23B). As seen in the image shown in FIG. 23A, it is apparent that the present invention improved the positional deviation and quantifying property as compared with the image shown in FIG. 22A obtained by the conventional method. The circle illustrated in FIG. 23A indicates the position of image expected.

The present invention makes it possible to obtain the reference value directly from the measured values for the measured object without obtaining the reference value from a physical model or a simulation model necessitated before and without using light having a plurality of wavelengths for one component in the measured object, and to image an internal property distribution (for example, an absorption coefficient change amount distribution, an absorption coefficient distribution, an absorptive constituent concentration distribution, a reduced scattering coefficient change amount distribution, a reduced scattering coefficient distribution, a refractive index change amount distribution, or a refractive index distribution) in the measured object based on the reference value. Therefore, the present invention can avoid occurrence of an error due to the difference between the actual measured object and the physical model or simulation model, the individual differences of measured object, or the like, thus permitting measurement with high reliability, i.e., with high accuracy. In addition, the present invention eliminates the need for the work to preliminarily obtain the reference value with the physical model or the like, thus enabling to decrease the measurement time. Further, the present invention can prevent occurrence of an error resulting from the assumption that the mean optical pathlength distribution and attenuation light quantity (the quantity of light attenuated due to influence of scattering or the like) are constant among plural wavelengths, thus enhancing the measurement accuracy.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Applications No. 140711/1996 filed on May 10, 1996, and No. 334674/1996 filed on Nov. 29, 1996 are hereby incorporated by reference.

What is claimed is:

1. A method for measuring an internal property distribution, comprising:
   making measurement light incident successively into a measurement object from a plurality of light incidence positions onto a surface of said measurement object;
   detecting the measurement light, said measurement light having passed through the measurement object successively or simultaneously, at at least one light detection position out of a plurality of light detection positions on the surface of said measurement object and in a predetermined positional relation with respect to a light incidence position at which the measurement light to be measured was incident;
   obtaining a measured value of a predetermined parameter of said measurement light based on incident measurement light detected at each light detection position;
   extracting a plurality of said measured values obtained by a plurality of combinations of said light incidence position and said light detection position, said positional relation of which is relatively identical, and calculating a mean value of the measured values to obtain a reference value in the positional relation; and
   calculating a change amount of a predetermined internal property in each region of said measurement object divided into a plurality of regions using said plurality of measured values obtained by said plurality of combinations, and said reference value, thereby obtaining an internal property change amount distribution in the measurement object.

2. A method for measuring an internal property distribution, comprising:
   making measurement light incident successively into a measurement object from a plurality of light incidence positions onto a surface of a said measurement object;
   detecting the measurement light, said measurement light having passed through the measurement object successively or simultaneously, at at least one light detection position out of a plurality of light detection positions on the surface of said measurement object and in a predetermined positional relation with respect to a light incidence position at which the measurement light to be measured was incident;
   obtaining a measured value of a predetermined parameter of said measurement light based on each incident measurement light detected at each light detection position;
   extracting a plurality of said measured values obtained by a plurality of combinations of said light incidence position and said light detection position, said positional relation of which is relatively identical, and calculating a mean value of the measured values to obtain a reference value in the positional relation; and
   calculating a change amount of a predetermined internal property in each region of said measurement object divided into a plurality of regions using said plurality of measured values obtained by said plurality of combinations, and said reference value, thereby obtaining an internal property change amount distribution of the measurement object,
   wherein said internal property is an absorption coefficient, said method further comprising:
      obtaining a mean absorption coefficient and a mean reduced scattering coefficient of said object; and
      selecting a spread function corresponding to said mean absorption coefficient and mean reduced scattering coefficient,
      wherein in said obtaining the internal property change amount distribution, a change amount of the absorption coefficient in said each region is calculated using said plurality of measured values, said reference value, and said spread function.

3. The method according to claim 2, wherein, in said step of obtaining said mean absorption coefficient and mean reduced scattering coefficient, said mean absorption coefficient and mean reduced scattering coefficient are obtained based on said reference value.

4. The method according to claim 2, further comprising calculating an absolute value of the absorption coefficient in said each region, using said change amount of the absorption coefficient and said mean absorption coefficient, and thereby obtaining an absorption coefficient absolute value distribution in said object.

5. The method according to claim 4, further comprising calculating a concentration of an absorptive constituent in said each region, using said absolute value of the absorption coefficient, and thereby obtaining an absorptive constituent concentration distribution in said object.

6. The method according to claim 5, wherein said object contains at least two absorptive constituents,
wherein the measurement light incident into said object in said light incidence step has at least two wavelengths at which absorption coefficients for the absorptive constituents are different from each other;
wherein, in said light detection, said measurement light having the at least two wavelengths is detected, respectively;
wherein, in said obtaining the measured values, said measured values are obtained for each of said measurement light having the at least two wavelengths;
wherein, in said obtaining the reference value, said mean value is calculated for each of said measurement light having the at least two wavelengths;
wherein, in said obtaining the internal property change amount distribution, the change amount of said absorption coefficient is calculated for each of said measurement light having the at least two wavelengths;
wherein, in said obtaining the absorption coefficient absolute value distribution, said absolute value of the absorption coefficient is calculated for each of said measurement light having the at least two wavelengths; and
wherein, in said obtaining the absorptive constituent concentration distribution, said concentration of the absorptive constituent is calculated for each of said measurement light having the at least two wavelengths, thereby obtaining a concentration distribution of said each absorptive constituent in said object.

7. A method for measuring an internal property distribution, comprising:
making measurement light incident successively into a measurement object from a plurality of light incidence positions onto a surface of a said measurement object;
detecting the measurement light, said measurement light having passed through the measurement object successively or simultaneously, at at least one light detection position out of a plurality of light detection positions on the surface of said measurement object and in a predetermined positional relation with respect to a light incidence position at which the measurement light to be measured was incident;
obtaining a measured value of a predetermined parameter of said measurement light based on each incident measurement light detected at each light detection position;
extracting a plurality of said measured values obtained by a plurality of combinations of said light incidence position and said light detection position, said positional relation of which is relatively identical, and calculating a mean value of the measured values to obtain a reference value in the positional relation; and
calculating a change amount of a predetermined internal property in each region of said measurement object divided into a plurality of regions using said plurality of measured values obtained by said plurality of combinations, and said reference value, thereby obtaining an internal property change amount distribution of the measurement object,
wherein said internal property is a reduced scattering coefficient,
said method further comprising:
obtaining a mean absorption coefficient and a mean reduced scattering coefficient of said measurement object; and
selecting a spread function corresponding to said mean absorption coefficient and mean reduced scattering coefficient,
wherein in said obtaining the internal property change amount distribution, a change amount of the reduced scattering coefficient in said each region is calculated using said plurality of measured values, said reference value, and said spread function.

8. The method according to claim 7, wherein, in said obtaining said means absorption coefficient and mean reduced scattering coefficient, said mean absorption coefficient and mean reduced scattering coefficient are obtained based on said reference value.

9. The method according to claim 7, further comprising calculating an absolute value of the reduced scattering coefficient in said each region, using the change amount of said reduced scattering coefficient and said mean reduced scattering coefficient, and thereby obtaining a reduced scattering coefficient absolute value distribution in said object.

10. A method for measuring an internal property distribution, comprising:
making measurement light incident successively into a measurement object from a plurality of light incidence positions onto a surface of a said measurement object;
detecting the measurement light, said measurement light having passed through the measurement object successively or simultaneously, at at least one light detection position out of a plurality of light detection positions on the surface of said measurement object and in a predetermined positional relation with respect to a light incidence position at which the measurement light to be measured was incident;
obtaining a measured value of a predetermined parameter of said measurement light based on each incident measurement light detected at each light detection position;
extracting a plurality of said measured values obtained by a plurality of combinations of said light incidence position and said light detection position, said positional relation of which is relatively identical, and calculating a mean value of the measured values to obtain a reference value in the positional relation; and
calculating a change amount of a predetermined internal property in each region of said measurement object divided into a plurality of regions using said plurality of measured values obtained by said plurality of combinations, and said reference value, thereby obtaining an internal property change amount distribution of the measurement object,
wherein said internal property is a refractive index,
said method further comprising:
obtaining a mean absorption coefficient, a mean reduced scattering coefficient, and a mean refractive index of said measurement object; and
selecting a spread function corresponding to said mean absorption coefficient, mean reduced scattering coefficient, and mean refractive index;

wherein in said obtaining the internal property change amount distribution, a change amount of the refractive index in said each region is calculated using said plurality of measured values, said reference value, and said spread function.

11. The method according to claim 10, wherein, in said obtaining said mean absorption coefficient, mean reduced scattering coefficient, and mean refractive index, at least the mean absorption coefficient and mean reduced scattering coefficient are obtained based on said reference value.

12. The method according to claim 10, further comprising calculating an absolute value of the refractive index in said each region, using said change amount of the refractive index and said mean refractive index, and thereby obtaining a refractive index absolute value distribution in said object.

13. A method for measuring an internal property distribution, comprising:

making measurement light incident successively into a measurement object from a plurality of light incidence positions onto a surface of a said measurement object;

detecting the measurement light, said measurement light having passed through the measurement object successively or simultaneously, at at least one light detection position out of a plurality of light detection positions on the surface of said measurement object and in a predetermined positional relation with respect to a light incidence position at which the measurement light to be measured was incident;

obtaining a measured value of a predetermined parameter of said measurement light based on each incident measurement light detected at each light detection position;

extracting a plurality of said measured values obtained by a plurality of combinations of said light incidence position and said light detection position, said positional relation of which is relatively identical, and calculating a mean value of the measured values to obtain a reference value in the positional relation; and calculating a change amount of a predetermined internal property in each region of said measurement object divided into a plurality of regions using said plurality of measured values obtained by said plurality of combinations, and said reference value, thereby obtaining an internal property change amount distribution of the measurement object, further comprising displaying an image indicating the distribution inside said measurement object, based on said distribution obtained.

14. An apparatus for measuring an internal property distribution, comprising:

light incidence means for making measurement light incident successively into a measurement object from a plurality of light incidence positions onto a surface of said measurement object;

light detection means for detecting the measurement light, said measurement light having passed though the measurement object successively or simultaneously, at at least one light detection position out of a plurality of light detection positions on the surface of the measurement object and in a predetermined positional relation with respect to a light incidence position at which the measurement light to be measured was incident;

measured value acquiring means for obtaining a measured value of a predetermined parameter of the measurement light based on each measurement light detected at each light detection position;

reference value calculating means for extracting a plurality of said measured values obtained by a plurality of combinations of said light incidence position and said light detection position said positional relation of which is relatively identical and calculating a mean value of the measured values to obtain a reference value in the positional relation; and internal property change amount calculating means for calculating a change amount of a predetermined internal property in each region of said object divided into a plurality of regions using said plurality of measured values obtained by said plurality of combinations, and said reference value, and thereby obtaining an internal property change amount distribution in the measurement object.

15. An apparatus for measuring an internal property distribution, comprising:

light incidence means for making measurement light incident successively into a measurement object from a plurality of light incidence positions onto a surface of said measurement object;

light detection means for detecting the measurement light, said measurement light having passed through the measurement object successively or simultaneously, at at least one light detection position out of a plurality of light detection positions on the surface of the measurement object and in a predetermined positional relation with respect to a light incidence position at which the measurement light to be measured was incident;

measured value acquiring means for obtaining a measured value of a predetermined parameter of the measurement light based on each measurement light detected at each light detection position;

reference value calculating means for extracting a plurality of said measured values obtained by a plurality of combinations of said light incidence position and said light detection position said positional relation of which is relatively identical and calculating a mean value of the measured values to obtain a reference value in the positional relation; and internal property change amount calculating means for calculating a change amount of a predetermined internal property in each region of said object divided into a plurality of regions using said plurality of measured values obtained by said plurality of combinations, and said reference value, and thereby obtaining an internal property change amount distribution in the object, wherein said internal property is an absorption coefficient, said apparatus further comprising:

mean absorption and scattering coefficient detecting means for obtaining a mean absorption coefficient and a mean reduced scattering coefficient of said object, and spread function selecting means for selecting a spread function corresponding to said mean absorption coefficient and mean reduced scattering coefficient;

wherein, in said internal property change amount calculating means, a change amount of the absorption coefficient in said each region is calculated using said plurality of measured values, said reference value, and said spread function.

16. The apparatus according to claim 15, wherein in said mean absorption and scattering coefficient detecting means, said mean absorption coefficient and mean reduced scattering coefficient are obtained based on said reference value.

17. The apparatus according to claim 15, further comprising absorption coefficient absolute value calculating means for calculating an absolute value of the absorption coefficient in said each region, using said change amount of the absorption coefficient and said mean absorption coefficient, and thereby obtaining an absorption coefficient absolute value distribution in said object.

18. The apparatus according to claim 17, further comprising absorptive constituent concentration calculating means for calculating a concentration of an absorptive constituent in said each region, using said absolute value of the absorption coefficient, and thereby obtaining an absorptive constituent concentration distribution in said object.

19. The apparatus according to claim 18, wherein said measurement object contains at least two absorptive constituents;
   wherein the measurement light incident into said object in said light incidence means has at least two wavelengths at which absorption coefficients for said absorptive constituents are different from each other;
   wherein in said light detection means said measurement light having the at least two wavelengths is detected respectively;
   wherein in said measured value acquiring means said measured values are obtained for each of said measurement light having the at least two wavelengths;
   wherein in said reference value calculating means said mean value is calculated for each of said measurement light having the at least two wavelengths;
   wherein in said internal property change amount calculating means said change amount of the absorption coefficient is calculated for each of said measurement light having the at least two wavelengths;
   wherein in said absorption coefficient absolute value calculating means said absolute value of the absorption coefficient is calculated for each of said measurement light having the at least two wavelengths; and
   wherein in said absorptive constituent concentration calculating means said concentration of the absorptive constituent is calculated for each of said measurement light having the at least two wavelengths, thereby obtaining a concentration distribution of said each absorptive constituent in said object.

20. An apparatus for measuring an internal property distribution, comprising:
   light incidence means for making measurement light incident successively into a measurement object from a plurality of light incidence positions onto a surface of said measurement object;
   light detection means for detecting the measurement light, said measurement light having passed through the measurement object successively or simultaneously, at at least one light detection position out of a plurality of light detection positions on the surface of the measurement object and in a predetermined positional relation with respect to a light incidence position at which the measurement light to be measured was incident;
   measured value acquiring means for obtaining a measured value of a predetermined parameter of the measurement light based on each measurement light detected at each light detection position;
   reference value calculating means for extracting a plurality of said measured values obtained by a plurality of combinations of said light incidence position and said light detection position said positional relation of which is relatively identical and calculating a mean value of the measured values to obtain a reference value in the positional relation; and
   internal property change amount calculating means for calculating a change amount of a predetermined internal property in each region of said object divided into a plurality of regions using said plurality of measured values obtained by said plurality of combinations, and said reference value, and thereby obtaining an internal property chance amount distribution in the object,
   wherein said internal property is a reduced scattering coefficient;
   said apparatus further comprising:
      mean absorption and scattering coefficient detecting means for obtaining a mean absorption coefficient and a mean reduced scattering coefficient of said object; and
      spread function selecting means for selecting a spread function corresponding to said mean absorption coefficient and mean reduced scattering coefficient;
      wherein, in said internal property change amount calculating means, a change amount of the reduced scattering coefficient in said each region is calculated using said plurality of measured values, said reference value, and said spread function.

21. The apparatus according to claim 20, wherein in said mean absorption and scattering coefficient detecting means, said mean absorption coefficient and mean reduced scattering coefficient are obtained based on said reference value.

22. The apparatus according to claim 20, further comprising reduced scattering coefficient absolute value calculating means for calculating an absolute value of the reduced scattering coefficient in said each region, using said change amount of the reduced scattering coefficient and said mean reduced scattering coefficient, and thereby obtaining a reduced scattering coefficient absolute value distribution in said object.

23. An apparatus for measuring an internal property distribution, comprising:
   light incidence means for making measurement light incident successively into a measurement object from a plurality of light incidence positions onto a surface of said measurement object;
   light detection means for detecting the measurement light, said measurement light having passed through the measurement object successively or simultaneously, at at least one light detection position out of a plurality of light detection positions on the surface of the measurement object and in a predetermined positional relation with respect to a light incidence position at which the measurement light to be measured was incident;
   measured value acquiring means for obtaining a measured value of a predetermined parameter of the measurement light based on each measurement light detected at each light detection position;
   reference value calculating means for extracting a plurality of said measured values obtained by a plurality of combinations of said light incidence position and said light detection position said positional relation of which is relatively identical and calculating a mean value of the measured values to obtain a reference value in the positional relation; and
   internal property change amount calculating means for calculating a change amount of a predetermined internal property in each region of said object divided into a plurality of regions using said plurality of measured values obtained by said plurality of combinations, and said reference value, and thereby obtaining an internal property change amount distribution in the object, wherein said internal property is a refractive index;

said apparatus further comprising:

mean absorption and scattering coefficient detecting means for obtaining a mean absorption coefficient, a mean reduced scattering coefficient, and a mean refractive index of said object; and spread function selecting means for selecting a spread function corresponding to said mean absorption coefficient, mean reduced scattering coefficient and mean refractive index;

wherein, in said internal property change amount calculating means, a change amount of the refractive index in said each region is calculated using said plurality of measured values, said reference value, and said spread function.

24. The apparatus according to claim 23, wherein in said mean absorption and scattering coefficient detecting means, at least said mean absorption coefficient and mean reduced scattering coefficient are obtained based on said reference value.

25. The apparatus according to claim 23, further comprising refractive index absolute value calculating means for calculating an absolute value of the refractive index in said each region, using said change amount of the refractive index and said mean refractive index, and thereby obtaining a refractive index absolute value distribution in said object.

26. An apparatus for measuring an internal property distribution, comprising:

light incidence means for making measurement light incident successively into a measurement object from a plurality of light incidence positions onto a surface of said measurement object;

light detection means for detecting the measurement light, said measurement light having passed through the measurement object successively or simultaneously, at at least one light detection position out of a plurality of light detection positions on the surface of the measurement object and in a predetermined positional relation with respect to a light incidence position at which the measurement light to be measured was incident;

measured value acquiring means for obtaining a measured value of a predetermined parameter of the measurement light based on each measurement light detected at each light detection position;

reference value calculating means for extracting a plurality of said measured values obtained by a plurality of combinations of said light incidence position and said light detection position said positional relation of which is relatively identical and calculating a mean value of the measured values to obtain a reference value in the positional relation; and internal property change amount calculating means for calculating a change amount of a predetermined internal property in each region of said object divided into a plurality of regions using said plurality of measured values obtained by said plurality of combinations, and said reference value, and thereby obtaining an internal property change amount distribution in the object, further comprising image display means for displaying an image indicating the distribution inside said object, based on said distribution obtained.

* * * * *